(12) United States Patent
Wu

(10) Patent No.: US 11,786,527 B2
(45) Date of Patent: Oct. 17, 2023

(54) PHARMACEUTICAL COMPOSITION AND PREPARATION METHOD THEREFOR AND USES THEREOF

(71) Applicant: WUXI SHUANGLIANG BIOTECHNOLOGY CO., LTD., Jiangsu (CN)

(72) Inventor: Jiaquan Wu, Wayland, MA (US)

(73) Assignee: WUXI SHUANGLIANG BIOTECHNOLOGY CO., LTD., Jiangsu (CN)

( * ) Notice: Subject to any disclaimer, the term of this patent is extended or adjusted under 35 U.S.C. 154(b) by 656 days.

(21) Appl. No.: 17/022,590

(22) Filed: Sep. 16, 2020

(65) Prior Publication Data

US 2021/0000828 A1    Jan. 7, 2021

Related U.S. Application Data

(63) Continuation of application No. PCT/CN2018/080326, filed on Mar. 23, 2018.

(51) Int. Cl.
| | | |
|---|---|---|
| *A61K 31/506* | (2006.01) | |
| *A61P 35/00* | (2006.01) | |
| *A61K 9/20* | (2006.01) | |

(52) U.S. Cl.
CPC .......... *A61K 31/506* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01)

(58) Field of Classification Search
CPC .............................. A61K 31/506; A61P 35/00
See application file for complete search history.

(56) References Cited

U.S. PATENT DOCUMENTS

| | | | |
|---|---|---|---|
| 10,183,020 | B2 | 1/2019 | Finnie et al. |
| 10,377,747 | B2 | 8/2019 | Wu et al. |
| 10,722,469 | B2 | 7/2020 | Lu et al. |
| 10,759,797 | B2 | 9/2020 | Zhou et al. |
| 2016/0324854 | A1 | 11/2016 | Finnie et al. |
| 2018/0208585 | A1 | 7/2018 | Wu et al. |
| 2019/0054025 | A1 | 2/2019 | Lu et al. |
| 2019/0111057 | A1 | 4/2019 | Finnie et al. |
| 2019/0194199 | A1 | 6/2019 | Zhou et al. |
| 2020/0360378 | A1 | 11/2020 | Finnie et al. |

FOREIGN PATENT DOCUMENTS

| | | |
|---|---|---|
| CN | 105848647 A | 8/2016 |
| CN | 106132957 A | 11/2016 |
| CN | 107176954 A | 9/2017 |
| CN | 107405345 A | 11/2017 |
| CN | 108938586 A | 12/2018 |
| EP | 3378479 A1 | 9/2018 |
| EP | 3502113 A1 | 6/2019 |
| WO | 2015/101791 A1 | 7/2015 |
| WO | 2017035753 A1 | 3/2017 |
| WO | 2017/129088 A1 | 8/2017 |
| WO | 2018218963 A1 | 12/2018 |

*Primary Examiner* — Bruck Kifle
(74) *Attorney, Agent, or Firm* — INNOVAR, L.L.C.; Rick Matos

(57) ABSTRACT

The present disclosure belongs to the field of pharmaceutical preparations, and discloses a pharmaceutical composition and a preparation method therefor and uses thereof. The pharmaceutical composition comprising EGFR inhibitor (C-005) and the pharmaceutical tablets prepared therefrom of the present disclosure are suitable for the treatment of cancer, preferably lung cancer, particularly non-small cell lung cancer.

19 Claims, 8 Drawing Sheets

PHARMACEUTICAL COMPOSITION AND PREPARATION METHOD THEREFOR AND USES THEREOF

CROSS-REFERENCE TO EARLIER FILED APPLICATIONS

This application claims the benefit of and is a continuation of PCT/CN2018/080326, filed Mar. 23, 2018, which claims the benefit of CN 201880002478.4, filed Mar. 23, 2018, the entire disclosures of which are hereby incorporated by reference.

TECHNICAL FIELD OF THE INVENTION

The present disclosure belongs to the field of pharmaceutical preparations, and relates to a pharmaceutical composition, a preparation method of the pharmaceutical composition, and a medical use of the pharmaceutical composition.

BACKGROUND OF THE INVENTION

Non-small cell lung cancer (NSCLC) includes all cancers of lung epithelial cells except small cell lung cancer (SCLC) and accounts for about 80% of lung cancers. According to the statistical data from American Cancer Society (ACS), there are approximately 200,000 new cases of NSCLC patients in the United States each year, of which 65% or more of the cases are in stage III or stage IV at the time of diagnosis. Apart from the fact that some advanced NSCLCs may be surgically removed after induction therapy, most of them still need to be intervened by way of radiotherapy or chemotherapy. However, it needs to be particularly noted that, chemotherapeutic drugs have significant systemic toxicities and side effects, which may cause considerable pain to patients. Therefore, the search for targeting drugs with high efficiency and low toxicity will become an inevitable trend for the development of antitumor drugs.

Epidermal growth factor receptor (EGFR) is a member of the ErbB receptor family, which has become a popular target for the development of anticancer drugs. Clinical data indicates that certain mutant forms of EGFR will eventually lead to the resistance to therapies by using drugs such as gefitinib and erlotinib. In view of the importance of these mutations in resistance to EGFR-targeting therapies, it may be speculated that drugs capable of inhibiting mutant EGFR will be effective for cancer treatment. In addition, there is still an urgent need for compounds that exhibit relatively high inhibitory effect on mutant EGFR and have no obvious inhibitory effect on wild-type (WT) EGFR, and such compounds are more suitable for use as therapeutic agents for cancers (especially NSCLCs). AZD9291, developed and launched by AstraZeneca, is the first third-generation oral and irreversible EGFR mutation-selective inhibitor, which may be used to inhibit both activated form and resistant mutant form of EGFR. The competition for new drugs is rather fierce since the third-generation EGFR inhibitors have unique efficacy and there are extremely limited products launched in the market at present.

As disclosed in PCT/CN2015/088643, a series of derivatives of 2-arylaminopyridine, pyrimidine or triazine also have relatively high EGFR inhibitory activity while exhibiting relatively low inhibitory activity against WT EGFR. The compound as represented by Formula I is described in this patent application and is referred to as "C-005" with a chemical name of "N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide". C-005 is a member of the above-mentioned series of derivatives of 2-arylaminopyridine, pyrimidine or triazine. C-005 may be used to inhibit both activated form and resistant mutant form of EGFR while exhibiting relatively low inhibitory activity against WT EGFR. Furthermore, the preparation and characterization of a variety of salts and crystal forms of C-005 is disclosed in PCT/CN2018/070011. The follow-up research and development of the pharmaceutical preparations of C-005 based on the above-mentioned technical information will have important clinical significance and application prospects.

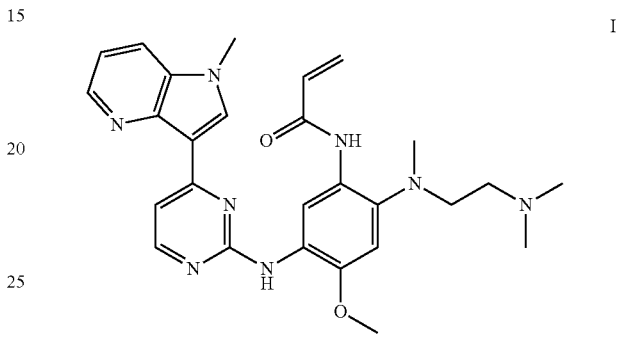

SUMMARY OF THE INVENTION

Problems to be Solved by the Disclosure

As is known to all, oral drugs may be absorbed at many different sites along the gastrointestinal tract (including stomach, duodenum, jejunum, ileum and colon) after administration. With the significant change of pH value between stomach (pH 1 to 3.5) and small intestine (pH 4 to 8), pH values may also be different at the above-mentioned absorption sites. As could be seen from the physical and chemical properties of C-005, C-005 has significant pH-dependent solubility and permeability. For example, it has been found that, compared to the solubility in aqueous solution (pH 7), C-005 in its free form has approximately 40 times higher solubility and C-005 mesylate even has more than 200 times higher solubility in a simulated gastric fluid (pH 1.2). In such cases, the solubility of the drug varies with pH and is highest under acidic conditions while being lowest under alkaline conditions, thus possibly causing the drug to precipitate out of the solution as it passes through the gastrointestinal tract. Since a drug needs to be present in a solution to enable its absorption, such precipitation may cause variability in the degree and/or rate of drug absorption, which may also result in that the amount of drug reaching the patient's systemic circulation varies significantly between one dose and the next dose in a given patient, and may also result in that the amount of drug reaching the patient's systemic circulation varies significantly between one patient and another patient. In principle, it is possible to adjust these differences by in-vivo monitoring or controlling the administration, however, it will definitely reduce the drug efficacy or increase the safety risk, as well as bringing additional economic burden and unfavorable clinical experience for the patients.

As for C-005 citrate, its solubility is significantly higher than that of C-005 in the free-base form under the pH conditions in intestine. Once formed, the solution of C-005 citrate appears to be stable and does not precipitate for a time period of at least 24 hours. Based on this, it is expected that a simple "blend in capsule" formed by C-005 citrate and microcrystalline cellulose will have favorable characteristics, including the rapid and complete dissolution within the physiological pH range, so as to avoid all the problems mentioned above. Unfortunately, however, the "blend in capsule" has a relatively long time limitation in terms of the expected destruction of the capsule shell, such that only 37% release is achieved after 30 minutes, 75% release is achieved after 60 minutes and 85% release is basically achieved after 120 minutes at pH 6.8. Therefore, there still remain certain problems in providing an improved way to administer drugs to patients, and the improved way should reduce/avoid the risk and/or severity of the above-mentioned problems caused by the inter-patient variability of absorption and/or the inter-dose variability of absorption.

The present disclosure provides solutions to one or more of the above-mentioned problems and relates to a novel pharmaceutical composition comprising a pharmaceutical substance. The pharmaceutical composition of the present disclosure may be in the form of a tablet, which exhibits improved dissolution characteristics under physiologically relevant conditions and/or a relatively high total release of the pharmaceutical substance under physiologically relevant conditions. It is expected that achieving a faster initial dissolution rate and/or a relatively high total release of the pharmaceutical substance will reduce the risk caused by the inter-dose and inter-patient variability of drug absorption. This drug has a pH-dependent solubility as demonstrated by C-005. Meanwhile, as could be seen from the screening of multiple formulations, among four dissolution media, i.e. a dissolution medium at pH 6.8, a dissolution medium at pH 4.5, water, and a dissolution medium at pH 1.2, the dissolution effect is the worst under a condition of pH 6.8. Therefore, a medium at the most rigorous pH (pH 6.8) and a medium at a moderate pH (pH 4.5) are generally selected as the media used for investigating the dissolution effect. In general, the dissolution effect becomes better as the dissolution time becomes shorter and the plateau level of dissolution is higher, and the dissolution effect needs to at least meet the requirement of being superior to that of the "blend in capsule".

Means for Solving the Problems

The pharmaceutical composition of the present disclosure exhibits significantly increased level of drug dissolution in a solution at pH 6.8 after 15, 30, and 60 minutes. The general procedure of the second method (paddle method) in General Rule 0931 of Chinese Pharmacopoeia (2015) is adopted, the average value of three dissolution percentages at pH 6.8 is obtained, and the data is as shown in the table below.

| Example No. | Dissolution (%) at corresponding time points | | | |
|---|---|---|---|---|
| | 15 min | 30 min | 45 min | 60 min |
| 1A | 33 | 58 | 71 | 85 |
| 1B | 31 | 53 | 69 | 80 |
| 1C | 77 | 81 | 83 | 85 |
| 2 | 50 | 79 | 79 | 78 |
| 3A | 58 | 57 | 57 | 56 |
| 3B | 80 | 85 | 84 | 83 |
| 3C | 13 | 23 | 36 | 50 |
| 4 | 84 | 83 | 82 | 82 |
| 5A | 84 | 84 | 84 | 84 |
| 5B | 84 | 85 | 85 | 84 |
| 5C | 86 | 86 | 87 | 86 |

-continued

| Example No. | Dissolution (%) at corresponding time points | | | |
|---|---|---|---|---|
| | 15 min | 30 min | 45 min | 60 min |
| 6A | 83 | 83 | 83 | 83 |
| 6B | 83 | 83 | 83 | 82 |
| 6C | 87 | 87 | 86 | 86 |
| 7 | 89 | 85 | 86 | 85 |
| 8A | 86 | 87 | 87 | 86 |
| 8B | 87 | 88 | 87 | 88 |
| 8C | 86 | 84 | 85 | 87 |
| 9 (Comparative example) | 16 | 37 | 64 | 75 |

It could be seen from the above table that, all examples except for Examples 1A, 1B, 2, 3A and 3C meet the requirement that the dissolution approaches or reaches 80% of the maximum dissolution within 15 minutes; Example 2 also meets the requirement that the dissolution approaches or reaches 80% of the maximum dissolution within 30 minutes; and Examples 1A and 1B also meet the requirement that the dissolution approaches or reaches 80% of the maximum dissolution within 60 minutes. In addition, most of the above-mentioned examples have achieved better dissolution effects than that of the "blend in capsule".

In the first aspect, provided in the present disclosure is a pharmaceutical composition comprising:
(a) from 3 to 70 parts of a pharmaceutical substance (or referred to as an active pharmaceutical ingredient, abbreviated as API);
(b) from 5 to 95 parts of one or more pharmaceutical diluents;
(c) from 0 to 50 parts of one or more pharmaceutical disintegrants;
(d) from 0 to 5 parts of one or more pharmaceutical solubilizers; and
(e) from 0 to 5 parts of one or more pharmaceutical lubricants;
wherein all parts are by weight and a sum of these parts in (a), (b), (c), (d) and (e) is 100; and
wherein the pharmaceutical substance is N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide or a pharmaceutically acceptable salt thereof.

In the present disclosure, "wt %" refers to "percentage by weight" and has its ordinary meaning in the art. Therefore, "wt %" refers to the proportion of Component X in Component Y comprising the same, and is calculated based on the weights of Component X and Component Y in each case (different from other physical parameters, such as the volume or the number of moles, if present). For example, if 2 g of Component X is contained in 20 g of Component Y, then Component X constitutes 10 wt % of Component Y.

In the present disclosure, by the wording "all parts are by weight" means that the amount of each component in the pharmaceutical composition is described by the unit "part(s)". It should be understood that such expression simply defines the relative proportions of these components, wherein said proportions are defined based on relative weights (different from other physical parameters, such as the volume or the number of moles, if present). For example, if a mixture contains 1 g of Component X and 4 g of Component Z, when the sum of the parts of Component X and Component Z is defined as 100, then in this example, the mixture contains 20 parts of Component X and 80 parts of Component Z.

Pharmaceutical Substance

Further, in the above-mentioned pharmaceutical composition, the pharmaceutical substance is a pharmaceutically acceptable salt of N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide, the pharmaceutically acceptable salt is an acid addition salt, and the acid is any one or more selected from the group consisting of hydrochloric acid, hydrobromic acid, sulfuric acid, phosphoric acid, trifluoroacetic acid, citric acid, maleic acid, fumaric acid, succinic acid, tartaric acid, lactic acid, pyruvic acid, oxalic acid, formic acid, acetic acid, benzoic acid, methanesulfonic acid, benzenesulfonic acid, and p-toluenesulfonic acid, preferably any one or more selected from the group consisting of hydrochloric acid, phosphoric acid, citric acid, methanesulfonic acid, and p-toluenesulfonic acid.

Still further, in the above-mentioned pharmaceutical composition, the pharmaceutical substance is N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide citrate disclosed in PCT/CN2018/070011, which has crystal form E and the X-ray powder diffraction (XRPD) pattern thereof has at least one characteristic peak at 2θ values of 5.4°±0.2°, 12.0°±0.2°, and 21.2°±0.2°, preferably further has at least one characteristic peak at 2θ values of 10.8°±0.2°, 17.5°±0.2°, 24.9°±0.2°, and 25.4°±0.2°, and more preferably further has at least one characteristic peak at 2θ values of 9.0°±0.2°, 12.4°±0.2°, 13.3°±0.2°, 16.0°±0.2°, and 20.4° ±0.2°.

Further, the pharmaceutical composition comprises the pharmaceutical substance (a) in an amount limited to any one of the ranges listed below:
from 3 to 70 parts by weight;
from 4 to 70 parts by weight;
from 4 to 65 parts by weight;
from 5 to 60 parts by weight;
from 6 to 60 parts by weight;
from 7 to 50 parts by weight;
from 8 to 45 parts by weight.
from 9 to 45 parts by weight; and
from 10 to 45 parts by weight.

Pharmaceutical Diluent

Further, in the above-mentioned pharmaceutical composition, the pharmaceutical diluent includes any one or more of microcrystalline cellulose, calcium phosphate, calcium sulfate, cellulose acetate (or referred to as acetyl cellulose), ethyl cellulose, erythritol, fructose, inulin, isomaltitol, lactitol, lactose, maltitol, maltodextrin, maltose, mannitol, sorbitol, polydextrose, polyethylene glycol, starch, sucrose, trehalose, and xylitol; preferably includes any one or more of microcrystalline cellulose, isomaltitol, lactitol, lactose, mannitol, sorbitol, and polydextrose; and more preferably includes any one or more of microcrystalline cellulose, mannitol, and lactose.

Further, the pharmaceutical composition comprises the pharmaceutical diluent (b) in an amount limited to any one of the ranges listed below:
from 5 to 95 parts by weight;
from 10 to 90 parts by weight;
from 10 to 85 parts by weight;
from 15 to 80 parts by weight;
from 15 to 70 parts by weight;
from 20 to 70 parts by weight.
from 30 to 70 parts by weight; and
from 40 to 70 parts by weight.

Still further, in the above-mentioned pharmaceutical composition, when the pharmaceutical diluent consists of one component, said one component is microcrystalline cellulose; and when the pharmaceutical diluent consists of multiple components, one of said multiple components is microcrystalline cellulose, the remaining component(s) include(s) any one or more of isomaltitol, lactitol, lactose, mannitol, sorbitol and polydextrose, and microcrystalline cellulose constitutes from 10 wt % to 90 wt %, preferably from 15 wt % to 90 wt %, and more preferably from 20 wt % to 90 wt %, of the pharmaceutical diluent (b).

Pharmaceutical Disintegrant

Further, in the above-mentioned pharmaceutical composition, the disintegrant includes any one or more of alginic acid, calcium alginate, sodium alginate, chitosan, calcium carboxymethylcellulose (CMC-Ca), sodium carboxymethylcellulose (CMC-Na), croscarmellose sodium (CCNa), povidone (PVP), crospovidone (or referred to as crosslinked polyvinylpyrrolidone, PVPP), guar gum, low-substituted hydroxypropyl cellulose (L-HPC), sodium carboxymethyl starch (CMS-Na), colloidal silica (or referred to as micronized silica gel, $SiO_2$), and starch, and preferably includes any one or more of low-substituted hydroxypropyl cellulose, sodium carboxymethyl starch, crospovidone, croscarmellose sodium, and colloidal silica.

Further, the pharmaceutical composition comprises the pharmaceutical disintegrant (c) in an amount limited to any one of the ranges listed below:
from 0 to 50 parts by weight;
from 0.5 to 45 parts by weight;
from 0.5 to 40 parts by weight;
from 0.5 to 30 parts by weight;
from 0.5 to 20 parts by weight;
from 0.5 to 15 parts by weight;
from 1 to 15 parts by weight; and
from 2 to 15 parts by weight.

Still further, in the above-mentioned pharmaceutical composition, when the pharmaceutical disintegrant consists of one component, said one component is crospovidone; and when the pharmaceutical disintegrant consists of multiple components, one of said multiple components is crospovidone, the remaining component(s) include(s) any one or more of low-substituted hydroxypropyl cellulose, sodium carboxymethyl starch, croscarmellose sodium and colloidal silica, and crospovidone constitutes from 10 wt % to 90 wt %, preferably from 15 wt % to 90 wt %, and more preferably from 20 wt % to 90 wt %, of the pharmaceutical disintegrant (c).

Still further, in the above-mentioned pharmaceutical composition, when the pharmaceutical disintegrant consists of one component, said one component is low-substituted hydroxypropyl cellulose; and when the pharmaceutical disintegrant consists of multiple components, one of said multiple components is low-substituted hydroxypropyl cellulose, the remaining component(s) include(s) any one or more of crospovidone, sodium carboxymethyl starch, croscarmellose sodium and colloidal silica, and low-substituted hydroxypropyl cellulose constitutes from 10 wt % to 90 wt %, preferably from 15 wt % to 90 wt %, and more preferably from 20 wt % to 90 wt %, of the pharmaceutical disintegrant (c).

Still further, in the above-mentioned pharmaceutical composition, when the pharmaceutical disintegrant consists of one component, said one component is sodium carboxymethyl starch; and when the pharmaceutical disintegrant consists of multiple components, one of said multiple components is sodium carboxymethyl starch, the remaining component(s) include(s) any one or more of crospovidone, low-substituted hydroxypropyl cellulose, croscarmellose sodium and colloidal silica, and the sodium carboxymethyl starch constitutes from 10 wt % to 50 wt %, preferably from 15 wt % to 50 wt %, and more preferably from 20 wt % to 50 wt %, of the pharmaceutical disintegrant (c).

Still further, in the above-mentioned pharmaceutical composition, when the pharmaceutical disintegrant consists of one component, said one component is colloidal silica; and when the pharmaceutical disintegrant consists of multiple components, one of said multiple components is colloidal silica, the remaining component(s) include(s) any one or more of crospovidone, low-substituted hydroxypropyl cellulose, croscarmellose sodium and sodium carboxymethyl starch, and colloidal silica constitutes from 10 wt % to 50 wt %, preferably from 15 wt % to 50 wt %, and more preferably from 20 wt % to 50 wt %, of the pharmaceutical disintegrant (c).

Pharmaceutical Solubilizer

Further, in the above-mentioned pharmaceutical composition, the solubilizer includes any one or more of benzalkonium chloride, benzyl benzoate, cetylpyridinium chloride (CPC), cyclodextrin, diethylene glycol monoethyl ether, lecithin, oleyl alcohol, poloxamer, sodium lauryl sulfate (SLS), sorbitan tristearate (ST), and glyceryl trioleate, preferably includes any one or more of sodium lauryl sulfate, cetylpyridinium chloride, and sorbitan tristearate, and more preferably includes sodium lauryl sulfate.

Further, the pharmaceutical composition comprises the pharmaceutical solubilizer (d) in an amount limited to any one of the ranges listed below:
  from 0 to 5 parts by weight;
  from 0 to 3 parts by weight;
  from 0 to 2 parts by weight;
  from 0 to 1 parts by weight; and
  from 0 to 0.5 parts by weight.

Still further, in the above-mentioned pharmaceutical composition, when the pharmaceutical solubilizer consists of one component, said one component is sodium lauryl sulfate; and when the pharmaceutical solubilizer consists of multiple components, one of said multiple components is sodium lauryl sulfate, the remaining component(s) include (s) any one or more of cetylpyridinium chloride and sorbitan tristearate, and sodium lauryl sulfate constitutes from 10 wt % to 90 wt %, preferably from 15 wt % to 90 wt %, and more preferably from 20 wt % to 90 wt %, of the pharmaceutical solubilizer (d).

Pharmaceutical Lubricant

Further, in the above-mentioned pharmaceutical composition, the lubricant includes any one or more of stearic acid, magnesium stearate, sodium stearate, calcium stearate, zinc stearate, glyceryl monobehenate, glyceryl dibehenate, glyceryl tribehenate, glyceryl monostearate, glyceryl distearate, glyceryl tristearate, myristic acid, palmitic acid, sodium stearyl fumarate, and talc, preferably includes any one or more of magnesium stearate, calcium stearate, myristic acid, palmitic acid, and sodium stearyl fumarate, and more preferably includes any one or more of magnesium stearate and sodium stearyl fumarate.

Further, the pharmaceutical composition comprises the pharmaceutical lubricant (e) in an amount limited to any one of the ranges listed below:
  from 0 to 5 parts by weight;
  from 0 to 4 parts by weight;
  from 0.5 to 4 parts by weight;
  from 0.8 to 3 parts by weight; and
  from 1 to 2 parts by weight.

Still further, in the above-mentioned pharmaceutical composition, when the pharmaceutical lubricant consists of one component, said one component is sodium stearyl fumarate; and when the pharmaceutical lubricant consists of multiple components, one of said multiple components is sodium stearyl fumarate, the remaining component(s) include(s) any one or more of magnesium stearate, calcium stearate, myristic acid and palmitic acid, and sodium stearyl fumarate constitutes from 10 wt % to 90 wt %, preferably from 15 wt % to 90 wt %, and more preferably from 20 wt % to 90 wt %, of the pharmaceutical lubricant (e).

Still further, in the above-mentioned pharmaceutical composition, when the pharmaceutical lubricant consists of one component, said one component is magnesium stearate; and when the pharmaceutical lubricant consists of multiple components, one of said multiple components is magnesium stearate, the remaining component(s) include(s) any one or more of sodium stearyl fumarate, calcium stearate, myristic acid and palmitic acid, and magnesium stearate constitutes from 10 wt % to 90 wt %, preferably from 15 wt % to 90 wt %, and more preferably from 20 wt % to 90 wt %, of the pharmaceutical lubricant (e).

In the second aspect, provided in the present disclosure is a preparation method of the above-mentioned pharmaceutical composition, which comprises a step of mixing a pharmaceutical substance, a diluent, a disintegrant, a solubilizer, and a lubricant.

In the third aspect, provided in the present disclosure is use of the above-mentioned pharmaceutical composition as a cancer therapeutic agent.

Further, in the above-mentioned use, the cancer is lung cancer, preferably non-small cell lung cancer, and more preferably advanced non-small cell lung cancer.

In the fourth aspect, provided in the present disclosure is the above-mentioned pharmaceutical composition, which is used as a cancer therapeutic agent.

Further, in the above-mentioned pharmaceutical composition, the cancer is lung cancer, preferably non-small cell lung cancer, and more preferably advanced non-small cell lung cancer.

In the fifth aspect, provided in the present disclosure is use of the above-mentioned pharmaceutical composition in the preparation of a pharmaceutical preparation for treating cancer.

Further, in the above-mentioned use, the cancer is lung cancer, preferably non-small cell lung cancer, and more preferably advanced non-small cell lung cancer.

In the sixth aspect, provided in the present disclosure is a pharmaceutical tablet comprising a tablet core, the tablet core comprises the above-mentioned pharmaceutical composition, preferably, the tablet core has a coating.

In the seventh aspect, provided in the present disclosure is a preparation method of the above-mentioned pharmaceutical tablet, which comprises the following steps: mixing each component comprised in the pharmaceutical composition; subjecting the mixture to dry granulating, sorting, tabletting and coating; and then obtaining the pharmaceutical tablet.

In the eighth aspect, provided in the present disclosure is use of the above-mentioned pharmaceutical tablet as a cancer therapeutic agent.

Further, in the above-mentioned use, the cancer is lung cancer, preferably non-small cell lung cancer, and more preferably advanced non-small cell lung cancer.

In the ninth aspect, provided in the present disclosure is the above-mentioned pharmaceutical tablet, which is used as a cancer therapeutic agent.

Further, in the above-mentioned pharmaceutical preparation, the cancer is lung cancer, preferably non-small cell lung cancer, and more preferably advanced non-small cell lung cancer.

In the tenth aspect, provided in the present disclosure is a method for treating cancer, which comprises a step of administering a therapeutically effective amount of the above-mentioned pharmaceutical composition or the above-mentioned pharmaceutical tablet to a cancer patient.

Further, in the above-mentioned method, the cancer is lung cancer, preferably non-small cell lung cancer, and more preferably advanced non-small cell lung cancer.

Further, in the above-mentioned method, the administration is oral administration.

Further, in the above-mentioned method, the patient is a mammalian patient, preferably a primate mammalian patient, and more preferably a human patient.

Advantageous Effects of the Disclosure

The pharmaceutical composition and the pharmaceutical tablet prepared therefrom of the present disclosure are capable of inhibiting mutant EGFR with high efficacy while exhibiting relatively low inhibitory activity against wild-type EGFR, thereby showing relatively high selectivity and improving the safety of drug administration. The pharmaceutical tablets of the present disclosure have relatively ideal disintegration time (most of the tablets are capable of realizing disintegration within 10 minutes, and some tablets even disintegrate within 1 to 3 minutes) and dissolution (most of the dissolution percentages are capable of reaching 80% or so and some of them even reach 90%, while most of the plateau levels of dissolution appear after about 15 to 20 minutes and some of them even appear after about 10 minutes), thus being suitable for being developed into a drug for treating cancer (preferably lung cancer, especially non-small cell lung cancer) and having important social and economic values.

DETAILED DESCRIPTION OF THE INVENTION

Figure 1:
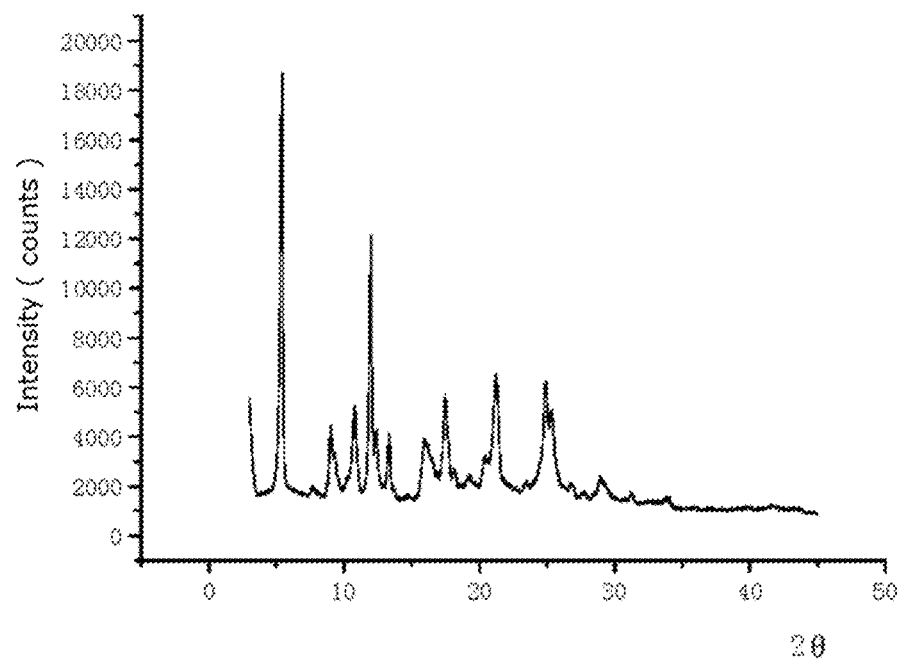
FIG. 1 shows the XRPD pattern of C-005 citrate in crystal form in the pharmaceutical composition or the pharmaceutical tablet of the present disclosure.

In the first aspect, provided in the present disclosure is a pharmaceutical composition. This pharmaceutical composition comprises:
(a) from 3 to 70 parts of a pharmaceutical substance;
(b) from 5 to 95 parts of one or more pharmaceutical diluents;
(c) from 0 to 50 parts of one or more pharmaceutical disintegrants;
(d) from 0 to 5 parts of one or more pharmaceutical solubilizers; and
(e) from 0 to 5 parts of one or more pharmaceutical lubricants;
wherein all parts are by weight and a sum of these parts in (a), (b), (c), (d) and (e) is 100; and
wherein this pharmaceutical substance is N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide or a pharmaceutically acceptable salt thereof.

Pharmaceutical Substance

In the context of the present disclosure, "pharmaceutical substance" refers to C-005 as represented by Formula I above or a pharmaceutically acceptable salt thereof, which is capable of exerting inhibitory activity on epidermal growth factor receptor (EGFR) and belongs to EGFR inhibitors.

Pharmaceutically Acceptable Salt

In the context of the present disclosure, "pharmaceutically acceptable salt" refers to a non-toxic acid addition salt formed by reacting an active pharmaceutical ingredient with an acid. The acids used to form this acid addition salt include not only inorganic acids, for example, hydrochloric acid, hydrobromic acid, sulfuric acid, phosphoric acid, and the like, but also organic acids, for example, trifluoroacetic acid, citric acid, maleic acid, fumaric acid, succinic acid, tartaric acid, lactic acid, pyruvic acid, oxalic acid, formic acid, acetic acid, benzoic acid, methanesulfonic acid, benzenesulfonic acid, p-toluenesulfonic acid, and the like.

In one embodiment of the present disclosure, the pharmaceutical substance in the above-mentioned pharmaceutical composition is any one or more selected from the group consisting of the hydrochloride, phosphate, citrate, mesylate and p-toluenesulfonate of C-005.

In one embodiment of the present disclosure, the pharmaceutical substance in the above-mentioned pharmaceutical composition is C-005 citrate. This citrate is capable of existing in amorphous or crystalline form.

C-005 citrate existed in crystalline form has crystal form E. The XRPD pattern of the crystal form E has at least one characteristic peak at 2θ values of 5.4°±0.2°, 12.0°±0.2°, and 21.2°±0.2°, preferably has at least one characteristic peak at 2θ values of 10.8°±0.2°, 17.5°±0.2°, 24.9°±0.2°, and 25.4°±0.2°, and more preferably has at least one characteristic peak at 2θ values of 9.0°±0.2°, 12.4°±0.2°, 13.3°±0.2°, 16.0°±0.2°, and 20.4°±0.2°.

In one embodiment of the present disclosure, the above-mentioned pharmaceutical composition may comprise the pharmaceutical substance (a) in an amount limited to any one of the ranges listed below:
from 3 to 70 parts by weight;
from 4 to 70 parts by weight;
from 4 to 65 parts by weight;
from 5 to 60 parts by weight;
from 6 to 60 parts by weight;
from 7 to 50 parts by weight;
from 8 to 45 parts by weight.
from 9 to 45 parts by weight; and
from 10 to 45 parts by weight.

Pharmaceutical Diluent

In the context of the present disclosure, "pharmaceutical diluent" (or referred to as "pharmaceutical filler") refers to a class of pharmaceutical excipients that are used to increase the weight or volume of a tablet to facilitate tabletting. Commonly used pharmaceutical diluents include starches, saccharides and sugar alcohols, celluloses, inorganic salts, and the like.

In one embodiment of the present disclosure, the pharmaceutical diluent in the above-mentioned pharmaceutical composition includes any one or more of microcrystalline cellulose, calcium phosphate, calcium sulfate, cellulose acetate, ethyl cellulose, erythritol, fructose, inulin, isomaltitol, lactitol, lactose, maltitol, maltodextrin, maltose, mannitol, sorbitol, polydextrose, polyethylene glycol, starch, sucrose, trehalose, and xylitol.

In one embodiment of the present disclosure, the pharmaceutical diluent in the above-mentioned pharmaceutical composition consists of one component, that is, microcrystalline cellulose.

In one embodiment of the present disclosure, the pharmaceutical diluent in the above-mentioned pharmaceutical composition consists of multiple components, one of the multiple components is microcrystalline cellulose, the remaining component(s) include(s) any one or more of isomaltitol, lactitol, lactose, mannitol, sorbitol and polydextrose, and microcrystalline cellulose constitutes from 10 wt % to 90 wt % of the pharmaceutical diluent (b).

In one embodiment of the present disclosure, the above-mentioned range is from 15 wt % to 90 wt %.

In one embodiment of the present disclosure, the above-mentioned range is from 20 wt % to 90 wt %.

In one embodiment of the present disclosure, the above-mentioned pharmaceutical composition may comprise the pharmaceutical diluent (b) in an amount limited to any one of the ranges listed below:
from 5 to 95 parts by weight;
from 10 to 90 parts by weight;
from 10 to 85 parts by weight;
from 15 to 80 parts by weight;
from 15 to 70 parts by weight;
from 20 to 70 parts by weight.
from 30 to 70 parts by weight; and
from 40 to 70 parts by weight.

Pharmaceutical Disintegrant

In the context of the present disclosure, "pharmaceutical disintegrant" refers to a class of pharmaceutical excipients that are used to enable a tablet to quickly break into fine particles in the digestive tract thereby enabling an active pharmaceutical ingredient to be quickly dissolved in the gastrointestinal fluid and absorbed by the subject. Commonly used pharmaceutical disintegrants include starch or the salts thereof, cellulose or the salts thereof, alginic acid or the salts thereof, povidones, and the like.

In one embodiment of the present disclosure, the pharmaceutical disintegrant in the above-mentioned pharmaceutical composition includes any one or more of alginic acid, calcium alginate, sodium alginate, chitosan, calcium carboxymethylcellulose, sodium carboxymethylcellulose, croscarmellose sodium, povidone, crospovidone, guar gum, low-substituted hydroxypropyl cellulose, sodium carboxymethyl starch, colloidal silica, and starch.

In one embodiment of the present disclosure, the pharmaceutical disintegrant in the above-mentioned pharmaceutical composition consists of one component, that is, crospovidone.

In one embodiment of the present disclosure, the pharmaceutical disintegrant in the above-mentioned pharmaceutical composition consists of multiple components, one of the multiple components is crospovidone, the remaining component(s) include(s) any one or more of low-substituted hydroxypropyl cellulose, sodium carboxymethyl starch, croscarmellose sodium and colloidal silica, and crospovidone constitutes from 10 wt % to 90 wt % of the pharmaceutical disintegrant (c).

In one embodiment of the present disclosure, the above-mentioned range is from 15 wt % to 90 wt %.

In one embodiment of the present disclosure, the above-mentioned range is from 20 wt % to 90 wt %.

In one embodiment of the present disclosure, the pharmaceutical disintegrant in the above-mentioned pharmaceutical composition consists of one component, that is, low-substituted hydroxypropyl cellulose.

In one embodiment of the present disclosure, the pharmaceutical disintegrant in the above-mentioned pharmaceutical composition consists of multiple components, one of the multiple components is low-substituted hydroxypropyl cellulose, the remaining component(s) include(s) any one or more of crospovidone, sodium carboxymethyl starch, croscarmellose sodium and colloidal silica, and low-substituted hydroxypropyl cellulose constitutes from 10 wt % to 90 wt % of the pharmaceutical disintegrant (c).

In one embodiment of the present disclosure, the above-mentioned range is from 15 wt % to 90 wt %.

In one embodiment of the present disclosure, the above-mentioned range is from 20 wt % to 90 wt %.

In one embodiment of the present disclosure, the pharmaceutical disintegrant in the above-mentioned pharmaceutical composition consists of one component, that is, sodium carboxymethyl starch.

In one embodiment of the present disclosure, the pharmaceutical disintegrant in the above-mentioned pharmaceutical composition consists of multiple components, one of the multiple components is sodium carboxymethyl starch, the remaining component(s) include(s) any one or more of crospovidone, low-substituted hydroxypropyl cellulose, croscarmellose sodium and colloidal silica, and sodium carboxymethyl starch constitutes from 10 wt % to 50 wt % of the pharmaceutical disintegrant (c).

In one embodiment of the present disclosure, the above-mentioned range is from 15 wt % to 50 wt %.

In one embodiment of the present disclosure, the above-mentioned range is from 20 wt % to 50 wt %.

In one embodiment of the present disclosure, the pharmaceutical disintegrant in the above-mentioned pharmaceutical composition consists of one component, that is, colloidal silica.

In one embodiment of the present disclosure, the pharmaceutical disintegrant in the above-mentioned pharmaceutical composition consists of multiple components, one of the multiple components is colloidal silica, the remaining component(s) include(s) any one or more of crospovidone, low-substituted hydroxypropyl cellulose, croscarmellose sodium and sodium carboxymethyl starch, and sodium carboxymethyl starch constitutes from 10 wt % to 50 wt % of the pharmaceutical disintegrant (c).

In one embodiment of the present disclosure, the above-mentioned range is from 15 wt % to 50 wt %.

In one embodiment of the present disclosure, the above-mentioned range is from 20 wt % to 50 wt %.

In one embodiment of the present disclosure, the above-mentioned pharmaceutical composition may comprise the pharmaceutical disintegrant (c) in an amount limited to any one of the ranges listed below:
from 0 to 50 parts by weight;
from 0.5 to 45 parts by weight;
from 0.5 to 40 parts by weight;
from 0.5 to 30 parts by weight;
from 0.5 to 20 parts by weight;
from 0.5 to 15 parts by weight;
from 1 to 15 parts by weight; and
from 2 to 15 parts by weight.

Pharmaceutical Solubilizer

In the context of the present disclosure, the term "pharmaceutical solubilizer" refers to a class of pharmaceutical excipients that are used to increase the solubility of a poorly soluble active pharmaceutical ingredient in a solution (generally, the gastrointestinal fluid under physiological conditions) so as to form a solution as clear as possible. Commonly used pharmaceutical solubilizers include alkyl sulfuric acid or the salts thereof, tetraalkylammonium halides, alkylpyridinium halides, cyclodextrins, polyethylene glycol monoethers, higher fatty alcohols, sugar alcohols or the fatty acid esters thereof, glycerin or the fatty acid esters thereof, and the like.

In one embodiment of the present disclosure, the pharmaceutical solubilizer in the above-mentioned pharmaceutical composition includes any one or more of benzalkonium chloride, benzyl benzoate, cetylpyridinium chloride, cyclodextrin, diethylene glycol monoethyl ether, lecithin, oleyl alcohol, poloxamer, sodium lauryl sulfate, sorbitan tristearate, and glyceryl trioleate.

In one embodiment of the present disclosure, the pharmaceutical solubilizer in the above-mentioned pharmaceutical composition consists of one component, that is, sodium lauryl sulfate.

In one embodiment of the present disclosure, the pharmaceutical solubilizer in the above-mentioned pharmaceutical composition consists of multiple components, one of the multiple components is sodium lauryl sulfate, the remaining component(s) include(s) any one or more of cetylpyridinium chloride and sorbitan tristearate, and sodium lauryl sulfate constitutes from 10 wt % to 90 wt % of the pharmaceutical solubilizer (d).

In one embodiment of the present disclosure, the above-mentioned range is from 15 wt % to 90 wt %.

In one embodiment of the present disclosure, the above-mentioned range is from 20 wt % to 90 wt %.

In one embodiment of the present disclosure, the above-mentioned pharmaceutical composition may comprise the pharmaceutical solubilizer (d) in an amount limited to any one of the ranges listed below:
from 0 to 5 parts by weight;
from 0 to 3 parts by weight;
from 0 to 2 parts by weight;
from 0 to 1 parts by weight; and
from 0 to 0.5 parts by weight.

Pharmaceutical Lubricant

In the context of the present disclosure, "pharmaceutical lubricant" is a lubricant in a narrow sense, which refers to a class of pharmaceutical excipients that are used to reduce the friction between tablets (or granules) and the die wall and/or punch of tablet machine so as to prevent the difficulty of tabletting and enable the tablets to have uniform and consistent density as well as smooth and flat surface. Commonly used pharmaceutical lubricants include higher fatty acids, higher fatty acid salts, higher fatty acid glycerides, polyacid fatty alcohol monoesters or the salts thereof, talc, and the like.

In one embodiment of the present disclosure, the pharmaceutical lubricant in the above-mentioned pharmaceutical composition includes any one or more of stearic acid, magnesium stearate, sodium stearate, calcium stearate, zinc stearate, glyceryl monobehenate, glyceryl dibehenate, glyceryl tribehenate, glyceryl monostearate, glyceryl distearate, glyceryl tristearate, myristic acid, palmitic acid, sodium stearyl fumarate, and talc.

In one embodiment of the present disclosure, the pharmaceutical lubricant in the above-mentioned pharmaceutical composition consists of one component, that is, sodium stearyl fumarate.

In one embodiment of the present disclosure, the pharmaceutical lubricant in the above-mentioned pharmaceutical composition consists of multiple components, one of the multiple components is sodium stearyl fumarate, the remaining component(s) include(s) any one or more of magnesium stearate, calcium stearate, myristic acid and palmitic acid, and sodium stearyl fumarate constitutes from 10 wt % to 90 wt % of the pharmaceutical lubricant (e).

In one embodiment of the present disclosure, the above-mentioned range is from 15 wt % to 90 wt %.

In one embodiment of the present disclosure, the above-mentioned range is from 20 wt % to 90 wt %.

In one embodiment of the present disclosure, the pharmaceutical lubricant in the above-mentioned pharmaceutical composition consists of one component, that is, magnesium stearate.

In one embodiment of the present disclosure, the pharmaceutical lubricant in the above-mentioned pharmaceutical composition consists of multiple components, one of the multiple components is magnesium stearate, the remaining component(s) include(s) any one or more of sodium stearyl fumarate, calcium stearate, myristic acid and palmitic acid, and magnesium stearate constitutes from 10 wt % to 90 wt % of the pharmaceutical lubricant (e).

In one embodiment of the present disclosure, the above-mentioned range is from 15 wt % to 90 wt %.

In one embodiment of the present disclosure, the above-mentioned range is from 20 wt % to 90 wt %.

In one embodiment of the present disclosure, the above-mentioned pharmaceutical composition may comprise the pharmaceutical lubricant (e) in an amount limited to any one of the ranges listed below:

from 0 to 5 parts by weight;
from 0 to 4 parts by weight;
from 0.5 to 4 parts by weight;
from 0.8 to 3 parts by weight; and
from 1 to 2 parts by weight.

In the second aspect, provided in the present disclosure is a preparation method of the above-mentioned pharmaceutical composition. This preparation method comprises a step of mixing a pharmaceutical substance, a diluent, a disintegrant, a solubilizer, and a lubricant.

In the third aspect, provided in the present disclosure is use of the above-mentioned pharmaceutical composition as a cancer therapeutic agent.

Cancer and Cancer Therapeutic Agent

In the context of the present disclosure, "cancer" generally refers to all malignant tumors, including brain cancer, nasopharyngeal cancer, esophageal cancer, gastric cancer, colorectal cancer, liver cancer, pancreatic cancer, lung cancer, bladder cancer, prostate cancer, breast cancer, bone cancer, blood cancer (leukemia, lymphoma, and myeloma), and the like. "Cancer therapeutic agent" refers to a pharmaceutical composition or a pharmaceutical preparation for treating cancer.

In one embodiment of the present disclosure, the cancer in the above-mentioned use is lung cancer.

In a preferred embodiment, the cancer in the above-mentioned use is non-small cell lung cancer.

In a more preferred embodiment, the cancer in the above-mentioned use is advanced non-small cell lung cancer.

In the fourth aspect, provided in the present disclosure is the above-mentioned pharmaceutical composition, which is used as a cancer therapeutic agent.

In one embodiment of the present disclosure, the above-mentioned pharmaceutical composition is used as a therapeutic agent for lung cancer.

In a preferred embodiment, the above-mentioned pharmaceutical composition is used as a therapeutic agent for non-small cell lung cancer.

In a more preferred embodiment, the above-mentioned pharmaceutical composition is used as a therapeutic agent for advanced non-small cell lung cancer.

In the fifth aspect, provided in the present disclosure is use of the above-mentioned pharmaceutical composition in the preparation of a pharmaceutical preparation for treating cancer.

In one embodiment of the present disclosure, the cancer in the above-mentioned use is lung cancer.

In a preferred embodiment, the cancer in the above-mentioned use is non-small cell lung cancer.

In a more preferred embodiment, the cancer in the above-mentioned use is advanced non-small cell lung cancer.

In the sixth aspect, provided in the present disclosure is a pharmaceutical tablet. The pharmaceutical tablet comprises a tablet core, the tablet core comprises the above-mentioned pharmaceutical composition, preferably, the tablet core has a coating.

Coating

In the context of the present disclosure, "coating" refers to a multifunctional protective layer formed on the outer surface of an intermediate particle or a tablet core (or referred to as a plain tablet).

In a preferred embodiment, the coating in the above-mentioned pharmaceutical tablet is prepared by using a series of coating materials under the brand name of Opadry®.

In the seventh aspect, provided in the present disclosure is a preparation method of the above-mentioned pharmaceutical tablet. This preparation method comprises the following steps: mixing each component comprised in the above-mentioned pharmaceutical composition; subjecting the mixture to dry granulating, sorting, tabletting and coating; and then obtaining the pharmaceutical tablet.

In the eighth aspect, provided in the present disclosure is use of the above-mentioned pharmaceutical tablet as a cancer therapeutic agent.

In one embodiment of the present disclosure, the cancer in the above-mentioned use is lung cancer.

In a preferred embodiment, the cancer in the above-mentioned use is non-small cell lung cancer.

In a more preferred embodiment, the cancer in the above-mentioned use is advanced non-small cell lung cancer.

In the ninth aspect, provided in the present disclosure is the above-mentioned pharmaceutical tablet, which is used as a cancer therapeutic agent.

In one embodiment of the present disclosure, the above-mentioned pharmaceutical tablet is used as a therapeutic agent for lung cancer.

In a preferred embodiment, the above-mentioned pharmaceutical tablet is used as a therapeutic agent for non-small cell lung cancer.

In a more preferred embodiment, the above-mentioned pharmaceutical tablet is used as a therapeutic agent for advanced non-small cell lung cancer.

In the tenth aspect, provided in the present disclosure is a method for treating cancer. This method comprises a step of administering a therapeutically effective amount of the above-mentioned pharmaceutical composition or the above-mentioned pharmaceutical tablet to a cancer patient.

Therapeutically Effective Amount

In the context of the present disclosure, "therapeutically effective amount" refers to the amount of a biologically active substance that is capable of achieving any one of the following effects: (1) preventing or treating a specific disease, condition or disorder; (2) alleviating, improving or eliminating one or more symptoms of a specific disease, condition or disorder; or (3) preventing or delaying the onset of one or more symptoms of a specific disease, condition or disorder.

Administration

In the context of the present disclosure, "administration" (or referred to as drug administration) refers to a behavior of administering an active pharmaceutical ingredient, a prodrug, a pharmaceutical composition or a pharmaceutical preparation (for example, the pharmaceutical composition or the pharmaceutical preparation of the present disclosure) to a patient (including a subject, an in-vivo/in-vitro/ex-vivo cell, tissue or organ). Common administration modes (or referred to as administration routes) include oral administration, skin administration (including topical administration, transdermal administration, and the like), ocular administration, nasal administration, pulmonary administration, mucosal administration (including intra-oral administration, intra-aural administration, vaginal administration, rectal administration, and the like), injection administration (including administration via intravenous injection, administration via subcutaneous injection, administration via intramuscular injection, and the like), and the like.

In one embodiment of the present disclosure, the administration in the above-mentioned method is oral administration.

In one embodiment of the present disclosure, the cancer in the above-mentioned method is lung cancer.

In a preferred embodiment, the cancer in the above-mentioned method is non-small cell lung cancer.

In a more preferred embodiment, the cancer in the above-mentioned method is advanced non-small cell lung cancer.

Patient

In the context of the present disclosure, "patient" refers to an object (including not only a whole/macroscopic object such as a subject, but also a partial/microscopic object such as an in-vivo/in-vitro/ex-vivo cell, tissue or organ) that has suffered from or will suffer from a specific disease. In the present disclosure, a patient may be not only a human patient, but also other animal patients (for example, fishes, amphibians, reptiles, birds, and mammals).

In one embodiment of the present disclosure, the patient in the above-mentioned method is a mammalian patient.

In a preferred embodiment, the patient in the above-mentioned method is a primate mammalian patient.

In a more preferred embodiment, the patient in the above-mentioned method is a human patient.

The technical solutions of the present disclosure will be further illustrated below in conjunction with specific examples. It should be understood that the following examples are merely provided for explaining and illustrating the present disclosure and are not intended to limit the protection scope of the present disclosure. Unless otherwise specified, all the instruments (as shown in Table 1), materials, reagents and the like used in the following examples may be obtained by conventional commercial means.

TABLE 1

Experimental equipments used in the examples of the present disclosure

| Equipment name | Manufacturer | Mode |
| --- | --- | --- |
| electronic balance | METTLER-TOLEDU | ME203E |
| electronic balance | METTLER-TOLEDU | ME3002E |
| electronic balance | METTLER-TOLEDU | PL203 |
| electronic balance | METTLER-TOLEDU | PL4001 |
| angle of repose tester | China Research Institute of Daily Chemical Industry | AR-1 |
| tap density tester | Tianjin Tianda Tianfa Technology Co., Ltd. | ES-2E |
| Comil ® milling and sorting machine | Quadro Engineering Corp. | U5 |
| dry granulator | Zhangjiagang Kaichuang Machinery Manufacturing Co., Ltd. | GL25 |
| tablet machine | Beijing Gylongli Sci. & Tech. Co., Ltd. | ZP10A |
| friability tester | Shanghai Huanghai Drug Testing Instrument Co., Ltd. | CJY-300B |
| hardness tester | Tianjin Tianda Tianfa Technology Co., Ltd. | YD-35 |
| disintegration tester | Shanghai Huanghai Drug Testing Instrument Co., Ltd. | LB-2D |
| sieve shaker | Shanghai Chemlab Laboratory Instrument Co., Ltd. | EML300 |
| coating machine | Zhejiang Xiaolun Pharmaceutical Machinery Co., Ltd. | BGB-5F |

Example 1: Ordinary Tablets (Specification: 50 Mg)

Tabletting was conducted in accordance with Formulations 1A to 1C in Table 2, so as to obtain Plain tablets 1A to 1C.

TABLE 2

Formulation lists of Plain tablets 1A to 1C

| Name of raw material and excipients | Manufacturer | Batch No. | mg/tablet | wt % | Theoretical amount (g) 200 tablets/ batch |
|---|---|---|---|---|---|
| Formulation No. 1A (Specification: 50 mg) | | | | | |
| *Inner portion* | | | | | |
| API[b] (C-005 citrate) | Self-produced | SLB-F170829 | 69.2[a] | 26.67% | 13.84 |
| mannitol | Merck & Co. Inc. | M809594 | 132.8 | 51.17% | 26.56 |
| microcrystalline cellulose (MCC PH102) | JRS Pharma | 5610264526 | 37.5 | 14.45% | 7.50 |
| low-substituted hydroxypropyl cellulose (L-HPC) | Shin-Etsu Chemical Co., Ltd. | 6121472 | 12.5 | 4.81% | 2.50 |
| sodium stearyl fumarate | Standard Chem. & Pharm. CO., LTD. | S96-0607 | 5.0 | 1.93% | 1.00 |
| Total of inner portion | | | 257.0 | 99.04 | 51.40 |
| *Outer portion* | | | | | |
| sodium stearyl fumarate | Standard Chem. & Pharm. CO., LTD. | S96-0607 | 2.5 | 0.96% | 0.50 |
| Total of outer portion | | | 2.5 | 0.96% | 0.50 |
| Total of inner and outer portions | | | 259.5 | 100.00% | 51.90 |
| Formulation No. 1B (Specification: 50 mg) | | | | | |
| *Inner portion* | | | | | |
| API (C-005 citrate) | Self-produced | SLB-F170829 | 69.2 | 26.93% | 13.84 |
| lactose monohydrate | DFE Pharma | 100M3MM | 134.0 | 52.14% | 26.80 |
| microcrystalline cellulose (MCC PH102) | JRS Pharma | 5610264526 | 37.5 | 14.59% | 7.50 |
| low-substituted hydroxypropyl cellulose (L-HPC) | Shin-Etsu Chemical Co., Ltd. | 6121472 | 12.5 | 4.86% | 2.50 |
| magnesium stearate | Faci Chemicals Co., Ltd. | MGS-R0317 | 1.3 | 0.51% | 0.26 |
| Total of inner portion | | | 254.5 | 99.03% | 50.90 |

TABLE 2-continued

Formulation lists of Plain tablets 1A to 1C

Outer portion

| | | | mg/tablet | wt % | Theoretical amount (g) 200 tablets/batch |
|---|---|---|---|---|---|
| magnesium stearate | Faci Chemicals Co., Ltd. | MGS-R0317 | 2.5 | 0.97% | 0.50 |
| Total of outer portion | | | 2.5 | 0.97% | 0.50 |
| Total of inner and outer portions | | | 257.0 | 100.00% | 51.40 |

Formulation No. 1C (Specification: 50 mg)

| Name of raw material and excipients | Manufacturer | Batch No. | mg/tablet | wt % | Theoretical amount (g) 200 tablets/batch |
|---|---|---|---|---|---|
| Inner portion | | | | | |
| API (C-005 citrate) | Self-produced | SLB-F170829 | 69.2 | 27.68% | 13.84 |
| lactose monohydrate | DFE Pharma | 100M3MM | 57.0 | 22.80% | 11.40 |
| microcrystalline cellulose (MCC PH102) | JRS Pharma | 5610264526 | 100.0 | 40.00% | 20.00 |
| sodium carboxymethyl starch (CMS-Na) | Yung Zip Chemical Ind. Co., Ltd. | SSG2015004 | 20.0 | 8.00% | 4.00 |
| magnesium stearate | Faci Chemicals Co., Ltd. | MGS-R0317 | 1.3 | 0.52% | 0.26 |
| Total of inner portion | | | 247.5 | 99.00% | 49.50 |
| Outer portion | | | | | |
| magnesium stearate | Faci Chemicals Co., Ltd. | MGS-R0317 | 2.5 | 1.00% | 0.50 |
| Total of outer portion | | | 2.5 | 1.00% | 0.50 |
| Total | | | 250.0 | 100.00% | 50.00 |

[a] Equivalent to 50 mg of C-005 in the form of free base;
[b] i.e., active pharmaceutical ingredients or raw material, also referred to as pharmaceutical substance. The same applied to the following content.

Preparation Processes 1A to 1C (1) The raw material was sieved through an 80-mesh sieve and all excipients were sieved through a 60-mesh sieve for later use.
(2) The formulated amount of the API (C-005 was prepared in accordance with the method described in Example 12 in the specification of PCT/CN2015/088643, and its citrate with crystal form E was prepared in accordance with the method described in Example 6 in the specification of PCT/CN2018/070011), the diluent, and the disintegrant were weighed, charged into the same ziplock bag and uniformly mixed.
(3) The formulated amount of the lubricant was weighed, and the lubricant for use as the inner portion was charged into the above-mentioned ziplock bag and uniformly mixed with the mixture therein.
(4) Dry granulating was carried out with a pressure of 3 MPa and a feed rate of 10 rpm.
(5) Comil U5 was used for sorting, a B040G03122* (1016) sieve was used for sieving, and the rotating speed was 2191 rpm.
(6) The granules and the lubricant for use as the outer portion were charged into the same ziplock bag and uniformly mixed with the mixture therein.
(7) Tabletting was conducted by using a Ø9 mm shallow arc punch. In Preparation process 1A, the tablet had a weight of 260 mg and a hardness of 30 N, the main pressure was 8.8 KN, and the rotating speed was 10 rpm. In Preparation process 1B, the tablet had a tablet weight of 257 mg and a hardness of 30N, the main pressure was 9.7 KN, and the rotating speed was 10 rpm. In Preparation process 1C, the tablet had a tablet weight of 250 mg and a hardness of 30N, the main pressure was 9.5 KN, and the rotating speed was 10 rpm. The tablet thickness, friability and disintegration time were determined.

TABLE 3

Test results of the tablet thickness, friability, and
disintegration time of Plain tablets 1A to 1C

| No. | Tablet weight | Hardness | Tablet thickness | Main pressure | Friability | Disintegration time |
|---|---|---|---|---|---|---|
| 1A | 260 mg | 30 N | 4.67 mm | 8.8 KN | 0.19% | 19 min |
| 1B | 257 mg | 30 N | 4.23 mm | 9.7 KN | 0.23% | 18 min |
| 1C | 250 mg | 30 N | 4.21 mm | 9.5 KN | 0.12% | 1 min 41 s |

Similar to AZD9291, C-005 also exhibited significant pH-dependent solubility, and it was therefore necessary to investigate its dissolution in a variety of media. Four media, i.e., water, a solution at pH 1.2 (hereinafter simply referred to as pH 1.2), a solution at pH 4.5 (hereinafter simply referred to as pH 4.5) and a solution at pH 6.8 (hereinafter simply referred to as pH 6.8), were selected for the investigation. Among these, pH 6.8 was relatively close to the dissolution environment of a pharmaceutical substance when the pharmaceutical substance was absorbed in vivo, and the pharmaceutical tablets were capable of exhibiting significantly increased level of drug dissolution at 15, 30 and 60 minutes under conditions of pH 4.5 and pH 6.8, therefore, the dissolution in these two media had more reference value. The dissolution data was obtained in accordance with the paddle method described in Chinese Pharmacopoeia (CP), specifically the second method in General Rule 0931 of CP2015.

The preparation method of the dissolution media was as described below.

(1) The solution at pH 1.2:45.9 mL of hydrochloric acid was measured and added into 6 L of degassed water, the mixture was stirred and uniformly mixed, and the above solution was obtained;

(2) The solution at pH 4.5:17.8 g of sodium acetate was weighed and added into 6 L of degassed water, 9.5 mL of acetic acid was then added after the dissolution of sodium acetate, the mixture was stirred and uniformly mixed, and the above solution was obtained;

(3) The solution at pH 6.8:40.83 g of potassium dihydrogen phosphate and 5.4 g of sodium hydroxide were weighed and added into 6 L of degassed water, the mixture was stirred and uniformly mixed, and the above solution was obtained;

(4) Water: purified water.

Figure 2:
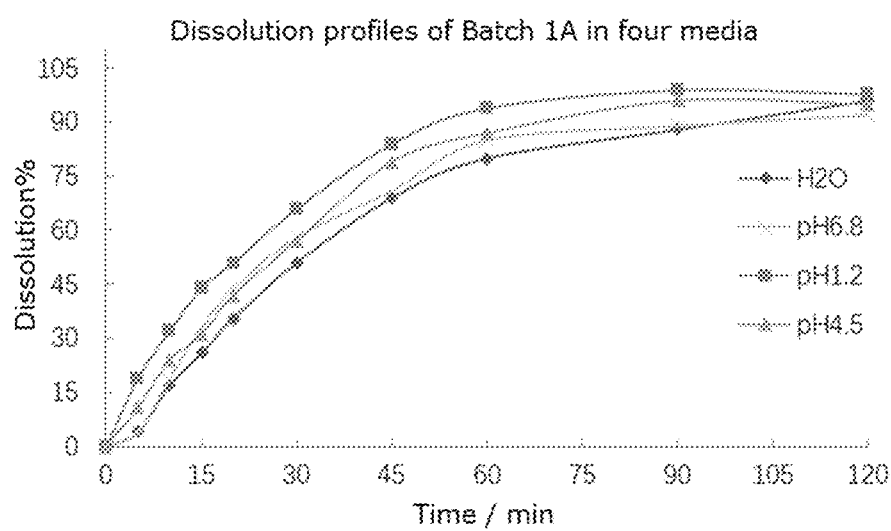
FIG. 2 shows the dissolution profiles of Plain tablet 1A in four dissolution media.
Figure 3:
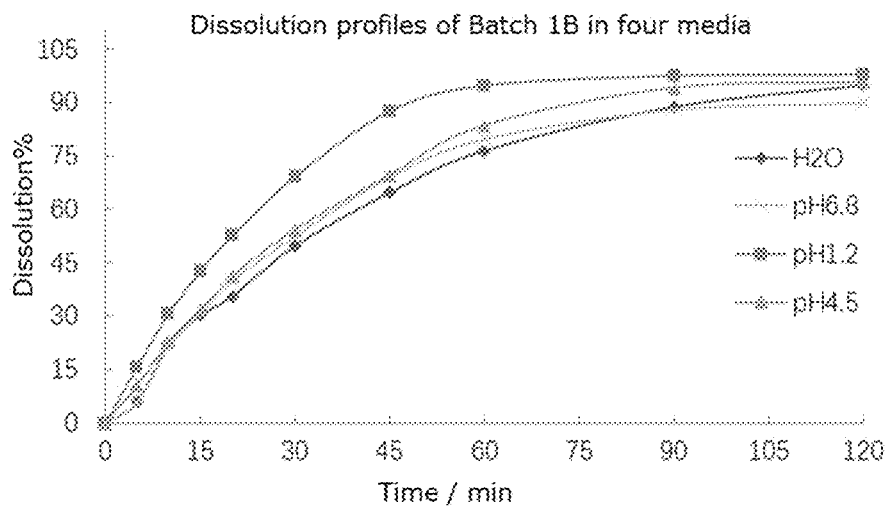
FIG. 3 shows the dissolution profiles of Plain tablet 1B in four dissolution media.
Figure 4:
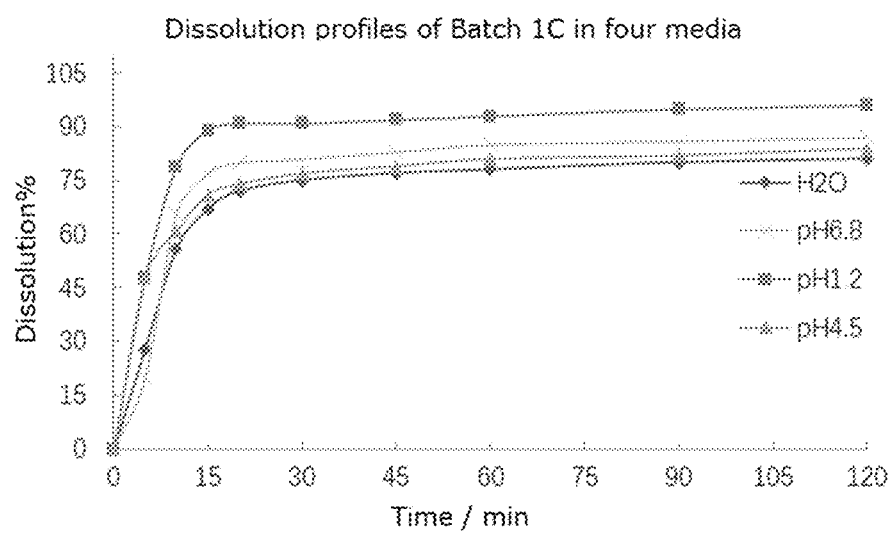
FIG. 4 shows the dissolution profiles of Plain tablet 1C in four dissolution media.

Dissolution method: The dissolution test was carried out at 37° C., 5.0 mL of sample was recovered from the dissolution medium at 0/5/10/15/20/30/45/60/90/120 minutes, filtered through the glass wool endremover filter (Acrodisc glass wool GxF (Component No. 4529) or its equivalent), and the first 2.5 ml of the filtrate was discarded. Quantification was carried out by UV analysis under a wavelength of 312 nm (ACE C18, 4.6*250 5 μm). Generally, the result of dissolution was the average value based on three repeated tests. The dissolution of the above-mentioned Plain tablets 1A to 1C was tested in four dissolution media (water, pH 1.2, pH 4.5 and pH 6.8), and the results were as shown in Table 4 and FIGS. 2 to 4.

TABLE 4

Test results of the dissolution of Plain tablets 1A to 1C

| Medium | No. | Time (mm) | | | | | | | | | |
|---|---|---|---|---|---|---|---|---|---|---|---|
| | | 0 | 5 | 10 | 15 | 20 | 30 | 45 | 60 | 90 | 120 |
| H₂O | 1A | 0 | 4 | 17 | 26 | 35 | 51 | 69 | 80 | 88 | 96 |
| | 1B | 0 | 6 | 22 | 30 | 35 | 50 | 65 | 76 | 89 | 95 |
| | 1C | 0 | 28 | 56 | 67 | 72 | 75 | 77 | 78 | 80 | 81 |
| pH 1.2 | 1A | 0 | 19 | 32 | 44 | 51 | 66 | 84 | 94 | 99 | 98 |
| | 1B | 0 | 16 | 31 | 42 | 53 | 69 | 88 | 95 | 98 | 98 |
| | 1C | 0 | 48 | 79 | 89 | 91 | 91 | 92 | 93 | 95 | 96 |
| pH 4.5 | 1A | 0 | 11 | 24 | 31 | 42 | 57 | 79 | 87 | 96 | 95 |
| | 1B | 0 | 10 | 23 | 32 | 41 | 54 | 70 | 84 | 94 | 96 |
| | 1C | 0 | 48 | 61 | 71 | 74 | 77 | 79 | 81 | 82 | 84 |
| pH 6.8 | 1A | 0 | 4 | 19 | 33 | 44 | 58 | 71 | 85 | 89 | 92 |
| | 1B | 0 | 6 | 21 | 31 | 40 | 53 | 69 | 80 | 88 | 90 |
| | 1C | 0 | 20 | 66 | 77 | 80 | 81 | 83 | 85 | 86 | 87 |

Example 2: Ordinary Tablets (Specification: 240 Mg)

Tabletting was conducted in accordance with Formulation 2 in Table 5, so as to obtain Plain tablet 2.

TABLE 5

Formulation list of Plain tablet 2

| Name of raw material and excipients | Manufacturer | Batch No. | Formulation No. 2 (Specification: 240 mg) | |
|---|---|---|---|---|
| | | | mg/tablet | wt % |
| Inner portion | | | | |
| API (C-005 citrate) | Self-produced | SLB-F170929-1 | 332.12[a] | 33.21% |
| colloidal silica ($SiO_2$) | EVONIK Corporation | 156021114 | 90.00 | 9.00% |
| low-substituted hydroxypropyl cellulose (L-HPC) | Shin-Etsu Chemical Co., Ltd. | 6121472 | 230.00 | 23.00% |
| sodium lauryl sulfate (SLS) | BASF Corporation | 0016990215 | 15.00 | 1.50% |
| Total of inner portion | | | 667.12 | 66.71% |
| Outer portion | | | | |
| microcrystalline cellulose (MCC PH102) | JRS Pharma | 5610264526 | 272.88 | 27.29% |
| low-substituted hydroxypropyl cellulose (L-HPC) | Shin-Etsu Chemical Co., Ltd. | 6121472 | 50.00 | 5.00% |
| magnesium stearate | Faci Chemicals Co., Ltd. | MGS-R0317 | 10.00 | 1.00% |
| Total of outer portion | | | 332.88 | 33.29% |
| Total of inner and outer portion | | | 1000.00 | 100.00% |

[a] Equivalent to 240 mg of C-005 in the form of free base

Preparation Process 2 (100 Tablets/Batch)

(1) The raw material was sieved through an 80-mesh sieve and all excipients were sieved through a 60-mesh sieve for later use.
(2) The formulated amount of the API, the solubilizer, and the disintegrant for use as the inner portion were weighed, charged into the same ziplock bag and uniformly mixed.
(3) Dry granulating was carried out with a pressure of 3 MPa, a feed rate of 10 rpm, and a rolling speed of 10 rpm.
(4) A 24-mesh sieve was used for dry sorting.
(5) The granules, the diluent, and the disintegrant for use as the outer portion were charged into the same ziplock bag and uniformly mixed with the mixture therein.
(6) Afterwards, the lubricant was charged into the same ziplock bag and uniformly mixed with the mixture therein.
(7) Tabletting was conducted by using a Ø20*10 mm capsule-shaped punch, the tablet weight was 999 mg, and the hardness was 130.1N. The tablet thickness, friability and disintegration time were determined.

TABLE 6

Test results of the tablet thickness, friability, and disintegration time of Plain tablet

| No. | Tablet weight | Tablet thickness | Hardness | Friability | Disintegration time |
|---|---|---|---|---|---|
| 2 | 999 mg | 6.61 mm | 130.1 N | 0.01% | 9 min |

Figure 5:
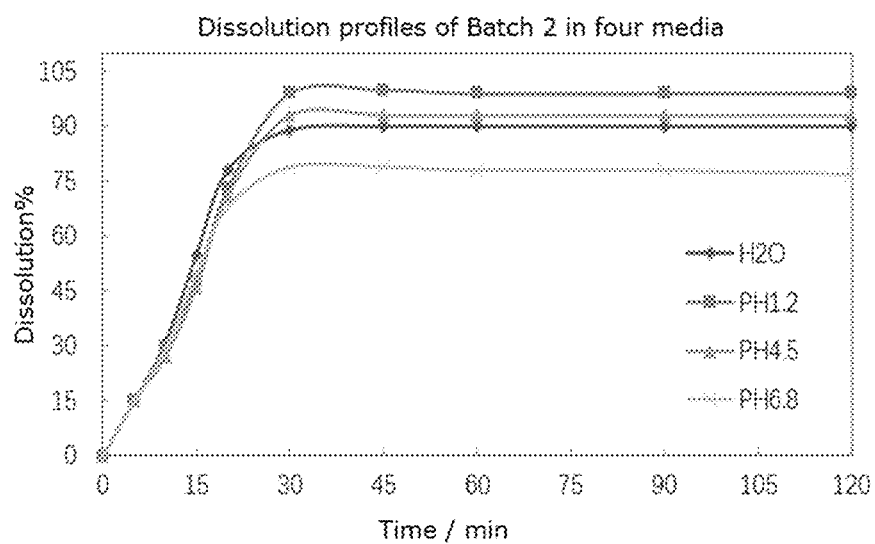
FIG. 5 shows the dissolution profiles of Plain tablet 2 in four dissolution media.

The dissolution of the above-mentioned Plain tablet 2 was tested in four dissolution media (water, pH 1.2, pH 4.5 and pH 6.8), and the results were as shown in Table 7 and FIG. 5.

TABLE 7

Test results of the dissolution of Plain tablet 2

| Medium | No. | Time (minutes) | | | | | | | | |
|---|---|---|---|---|---|---|---|---|---|---|
| | | 0 | 5 | 10 | 15 | 20 | 30 | 45 | 60 | 90 | 120 |
| $H_2O$ | 2 | 0 | 15 | 31 | 55 | 78 | 89 | 90 | 90 | 90 | 90 |
| pH 1.2 | 2 | 0 | 15 | 30 | 48 | 73 | 99 | 100 | 99 | 99 | 99 |
| pH 4.5 | 2 | 0 | 15 | 27 | 46 | 71 | 93 | 93 | 93 | 93 | 93 |
| pH 6.8 | 2 | 0 | 15 | 29 | 50 | 68 | 79 | 79 | 78 | 78 | 77 |

As could be seen from the results in Table 7, the plateau level of dissolution was reached after 30 minutes in the medium at pH 6.8, and the dissolution percentage could reach 80% or so; the plateau level of dissolution was also reached after 30 minutes in the other three media, and the dissolution percentage could reach 85% or higher.

Example 3: Ordinary Tablets Comprising Different Disintegrants (Specification: 240 Mg)

Tabletting was conducted in accordance with Formulations 3A to 3C in Table 8, so as to obtain Plain tablets 3A to 3C.

TABLE 8

Formulation lists of Plain tablets 3A to 3C

| Name of raw material and excipients | Formulation No. 3A (Specification: 240 mg) | | | |
|---|---|---|---|---|
| | Manufacturer | Batch No. | mg/tablet | wt % |
| Inner portion | | | | |
| API (C-005 citrate) | Self-produced | SLB-F17002 | 332.12[a] | 33.21% |
| colloidal silica ($SiO_2$) | EVONIK Corporation | 156021114 | 30.00 | 3.00% |
| microcrystalline cellulose (MCC PH102) | JRS Pharma | 5610274323 | 100.00 | 10.00% |
| croscarmellose sodium (CCNa) | FMC BioPolymer Corporation | TN17831072 | 50.00 | 5.00% |
| magnesium stearate | Faci Chemicals Co., Ltd. | MGS-R0317 | 10.00 | 1.00% |
| Total of inner portion | | | 522.12 | 52.21% |
| Outer portion | | | | |
| low-substituted hydroxypropyl cellulose (L-HPC) | Shin-Etsu Chemical Co., Ltd. | 6121472 | 50.00 | 5.00% |
| microcrystalline cellulose (MCC PH102) | JRS Pharma | 5610274323 | 407.88 | 40.79% |
| magnesium stearate | Faci Chemicals Co., Ltd. | MGS-R0317 | 20.00 | 2.00% |
| Total of outer portion | | | 477.88 | 47.79% |
| Total of inner and outer portion | | | 1000.00 | 100.00% |

TABLE 8-continued

Formulation lists of Plain tablets 3A to 3C

| Name of raw material and excipients | Formulation No. 3B (Specification: 240 mg) | | | |
|---|---|---|---|---|
| | Manufacturer | Batch No. | mg/tablet | wt % |
| Inner portion | | | | |
| API (C-005 citrate) | Self-produced | SLB-F17002 | 332.12 | 33.21% |
| colloidal silica (SiO$_2$) | EVONIK Corporation | 156021114 | 30.00 | 3.00% |
| microcrystalline cellulose (MCC PH102) | JRS Pharma | 5610274323 | 100.00 | 10.00% |
| crospovidone (PVPP) | Ashland Group Corporation | OOO1926358 | 80.00 | 8.00% |
| magnesium stearate | Faci Chemicals Co., Ltd. | MGS-R0317 | 10.00 | 1.00% |
| Total of inner portion | | | 552.12 | 55.21% |
| Outer portion | | | | |
| low-substituted hydroxypropyl cellulose (L-HPC) | Shin-Etsu Chemical Co., Ltd. | 6121472 | 50.00 | 5.00% |
| microcrystalline cellulose (MCC PH102) | JRS Pharma | 5610274323 | 387.88 | 38.79% |
| magnesium stearate | Faci Chemicals Co., Ltd. | MGS-R0317 | 10.00 | 1.00% |
| Total of outer portion | | | 478.88 | 47.89% |
| Total of inner and outer portion | | | 1000.00 | 100.00% |

| Name of raw material and excipients | Formulation No. 3C (Specification: 240 mg) | | | |
|---|---|---|---|---|
| | Manufacturer | Batch No. | mg/tablet | wt % |
| Inner portion | | | | |
| API (C-005 citrate) | Self-produced | SLB-F17002 | 332.12 | 33.21% |
| colloidal silica (SiO$_2$) | EVONIK Corporation | 156021114 | 10.00 | 1.00% |
| microcrystalline cellulose (MCC PH102) | JRS Pharma | 5610274323 | 100.00 | 10.00% |
| low-substituted hydroxypropyl cellulose (L-HPC) | Shin-Etsu Chemical Co., Ltd. | 6121472 | 10.00 | 1.00% |
| mannitol | Merck & Co., Inc. | M809594 | 110.00 | 11.00% |
| magnesium stearate | Faci Chemicals Co., Ltd. | MGS-R0317 | 10.00 | 1.00% |
| Total of inner portion | | | 572.12 | 57.21% |
| Outer portion | | | | |
| low-substituted hydroxypropyl cellulose (L-HPC) | Shin-Etsu Chemical Co., Ltd. | 6121472 | 40.00 | 4.00% |
| microcrystalline cellulose (MCC PH102) | JRS Pharma | 5610274323 | 372.88 | 37.29% |
| magnesium stearate | Faci Chemicals Co., Ltd. | MGS-R0317 | 15.00 | 1.50% |
| Total of outer portion | | | 427.88 | 42.79% |
| Total of inner and outer portion | | | 1000 | 100.00% |

[a] Equivalent to 240 mg of C-005 in the form of free base

Preparation Processes 3A to 3C (1) The raw material was sieved through an 80-mesh sieve and all excipients were sieved through a 60-mesh sieve for later use.
(2) The formulated amount of the API, the disintegrant for use as the inner portion, and the diluent for use as the inner portion were weighed, charged into the same ziplock bag, uniformly mixed, and then sieved by using a 60-mesh sieve for 3 times.
(3) The formulated amount of the lubricant for use as the inner portion was weighed and charged into the same ziplock bag together with the sieved materials in (2), and the resulting mixture was uniformly mixed.

(4) Dry granulating was carried out with a pressure of 3 MPa, a feed rate of 17 rpm, and a rolling speed of 10 rpm.
(5) The resulting mixture was sieved through a 24-mesh sieve.
(6) The formulated amount of the disintegrant for use as the outer portion and the diluent for use as the outer portion were weighed, both of them were charged into the same ziplock bag together with the dry granules, and the resulting mixture was uniformly mixed.
(7) The formulated amount of the lubricant for use as the outer portion was weighed, charged into the same ziplock bag and uniformly mixed with the mixture therein.
(8) Tabletting was conducted by using a 20*10 mm capsule-shaped punch. In Preparation process 3A, the tablet had a tablet weight of 1000 mg and a hardness of 154.2 N. In Preparation process 3B, the tablet had a tablet weight of 1000 mg and a hardness of 155.3 N. In Preparation process 3C, the tablet had a tablet weight of 1000 mg and a hardness of 166.4 N. The tablet thickness, friability and disintegration time were determined.

TABLE 9

Test results of the tablet thickness, friability, and disintegration time of Plain tablets 3A to 3C

| No. | Tablet weight | Thickness | Hardness | Friability | Disintegration time |
|---|---|---|---|---|---|
| 3A | 1000 mg | 6.53 mm | 154.2 N | 0.13% | 3 min 15 s |
| 3B | 1000 mg | 6.53 mm | 155.3 N | 0.16% | 10 min 58 s |
| 3C | 1000 mg | 6.39 mm | 166.4 N | 0.23% | 28 min 13 s |

Figure 6:
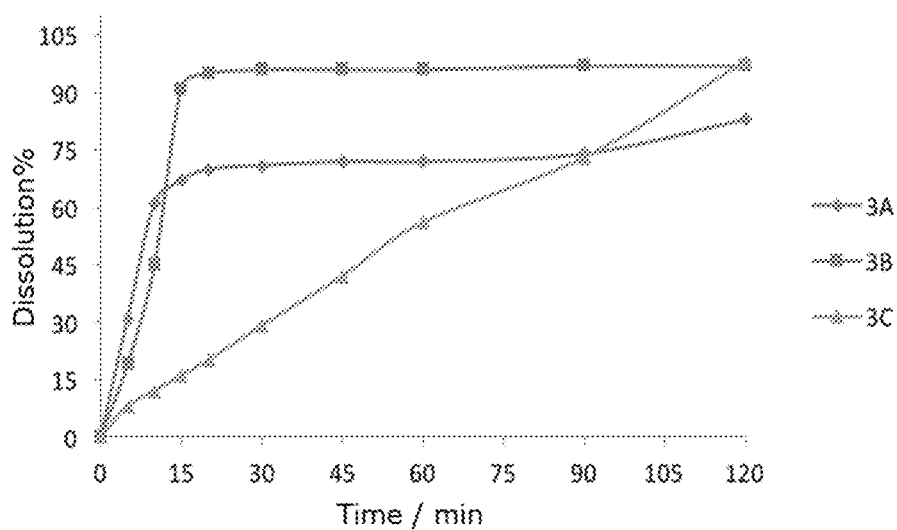
FIG. 6 shows the dissolution profiles of Plain tablets 3A to 3C in a dissolution medium at pH 4.5.
Figure 7:
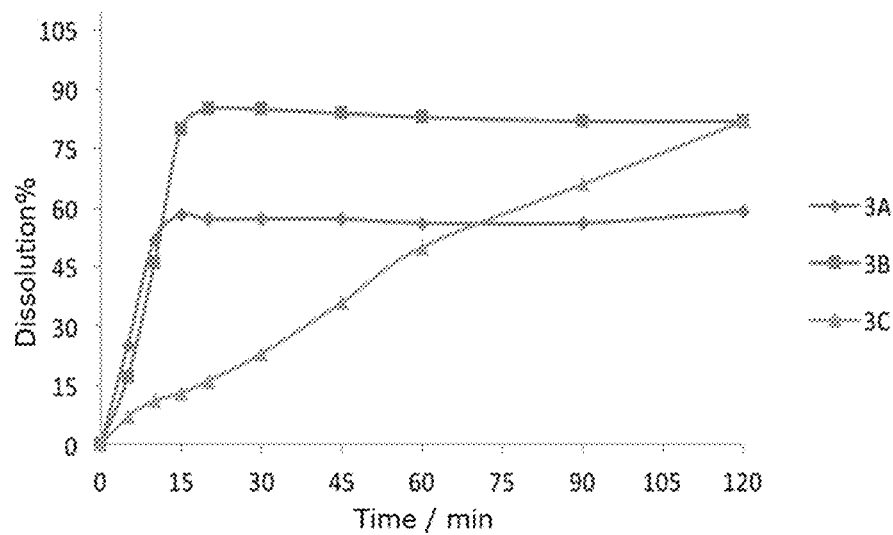
FIG. 7 shows the dissolution profiles of Plain tablets 3A to 3C in a dissolution medium at pH 6.8.

The dissolution of the above-mentioned Plain tablets 3A to 3C was tested in four dissolution media (water, pH 1.2, pH 4.5 and pH 6.8), and the results were as shown in Table 10 and FIGS. 6 to 7.

TABLE 10

Test results of the dissolution of Plain tablets 3A to 3C

| Medium | No. | Time (minutes) | | | | | | | | | |
|---|---|---|---|---|---|---|---|---|---|---|---|
| | | 0 | 5 | 10 | 15 | 20 | 30 | 45 | 60 | 90 | 120 |
| pH 4.5 | 3A | 0 | 31 | 61 | 67 | 70 | 71 | 72 | 72 | 74 | 83 |
| | 3B | 0 | 19 | 45 | 91 | 95 | 96 | 96 | 96 | 97 | 97 |
| | 3C | 0 | 8 | 12 | 16 | 20 | 29 | 42 | 56 | 73 | 98 |
| pH 6.8 | 3A | 0 | 25 | 52 | 58 | 57 | 57 | 57 | 56 | 56 | 59 |
| | 3B | 0 | 17 | 46 | 80 | 85 | 85 | 84 | 83 | 82 | 82 |
| | 3C | 0 | 7 | 11 | 13 | 16 | 23 | 36 | 50 | 66 | 82 |
| $H_2O$ | 3B | 0 | 16 | 40 | 80 | 94 | 95 | 95 | 95 | 95 | 95 |
| pH 1.2 | 3B | 0 | 20 | 40 | 79 | 98 | 98 | 98 | 98 | 98 | 98 |

As could be seen from the results in Table 10, Plain tablets 3A to 3C were mostly capable of reaching the plateau levels of dissolution in four media after 20 minutes. Among these, the dissolution percentage of Plain tablet 3B could reach 91% within 15 minutes in the medium at pH 4.5, reach 85% within 20 minutes and then reach the plateau level of dissolution in the medium at pH 6.8, and respectively reach the plateau level of dissolution after 20 minutes in water and the medium at pH 1.2.

Example 4: Ordinary Tablets Comprising Different Diluents (Specification: 240 Mg)

In Formulation 4 of this Example, MCC PH200 was used as a diluent instead of MCC PH102 in Formulation 3B. Tabletting was conducted in accordance with Formulation 4 in Table 11, so as to obtain Plain tablet 4.

TABLE 11

Formulation list of Plain tablet 4

| Name of raw material and excipients | Manufacturer | Formulation No. 4 (Specification: 240 mg) | | |
|---|---|---|---|---|
| | | Batch No. | mg/tablet | wt % |
| Inner portion | | | | |
| API (C-005 citrate) | Self-produced | SLB-F17002 | 332.12[a] | 33.21% |
| colloidal silica ($SiO_2$) | EVONIK Corporation | 156021114 | 30.00 | 3.00% |
| microcrystalline cellulose (MCC PH200) | FMC BioPolymer Corporation | PN14827536 | 100.00 | 10.00% |
| crospovidone (PVPP) | Ashland Group Corporation | OOO1926358 | 80.00 | 8.00% |
| magnesium stearate | Faci Chemicals Co., Ltd. | MGS-R0317 | 10.00 | 1.00% |
| Total of inner portion | | | 552.12 | 55.21% |
| Outer portion | | | | |
| low-substituted hydroxypropyl cellulose (L-HPC) | Shin-Etsu Chemical Co., Ltd. | 6121472 | 50.00 | 5.00% |
| microcrystalline cellulose (MCC PH200) | FMC BioPolymer Corporation | PN14827536 | 387.88 | 38.79% |
| magnesium stearate | Faci Chemicals Co., Ltd. | MGS-R0317 | 10.00 | 1.00% |
| Total of outer portion | | | 478.88 | 47.89% |
| Total of inner and outer portion | | | 1000.00 | 100.00% |

[a]Equivalent to 240 mg of C-005 in the form of free base

Preparation Process 4

(1) The raw material was sieved through an 80-mesh sieve and all excipients were sieved through a 60-mesh sieve for later use.
(2) The formulated amount of the API, the diluent for use as the inner portion, and the disintegrant for use as the inner portion were weighed, charged into the same ziplock bag, uniformly mixed, and then sieved by using a 60-mesh sieve for 3 times.
(3) The formulated amount of the lubricant for use as the inner portion was weighed and charged into the same ziplock bag together with the sieved materials in (2), and the resulting mixture was uniformly mixed.
(4) Dry granulating was carried out with a pressure of 3 MPa, a feed rate of 19 rpm, and a rolling speed of 20 rpm.
(5) The resulting mixture was sieved through a 24-mesh sieve.
(6) The formulated amount of the disintegrant for use as the outer portion and the diluent for use as the outer portion were weighed, both of them were charged into the same ziplock bag together with the dry granules, and the resulting mixture was uniformly mixed.
(7) The formulated amount of the lubricant for use as the outer portion was weighed, charged into the same ziplock bag and uniformly mixed with the mixture therein.
(8) Tabletting was conducted by using a 20*10 mm capsule-shaped punch. The tablet thickness, friability and disintegration time were determined.

TABLE 12

Test results of the tablet thickness, friability, and
disintegration time of two batches of Plain tablet 4

| No. | Tablet weight | Thickness | Hardness | Friability | Disintegration time | Phenomenon during tabletting |
|---|---|---|---|---|---|---|
| 4 | 1004 mg | 6.74 mm | 177.7 N | 0.10% | 3 min 55 s | No obvious sticking |
|   | 1001 mg | 6.74 mm | 164.3 N |  |  |  |
| Results obtained by rotating same plain tablets in a friability tester for 3 times |  |  |  | 0.53% |  |  |

Figure 8:
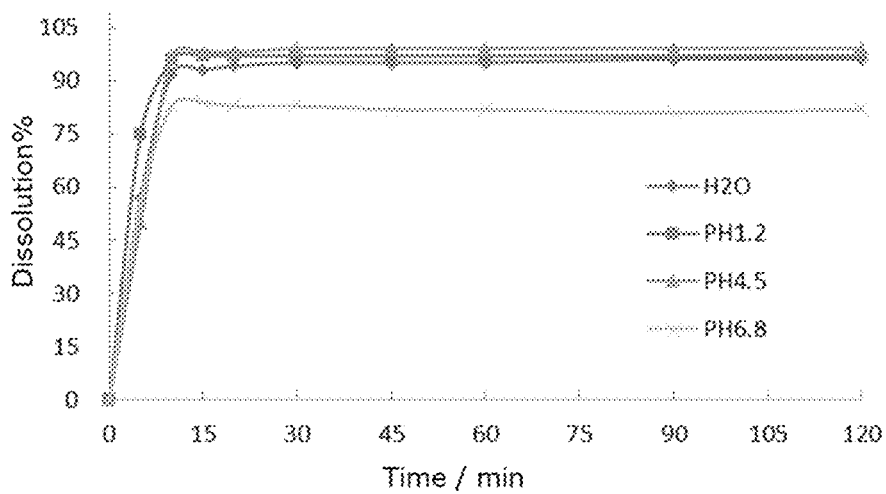
FIG. 8 shows the dissolution profiles of Plain tablet 4 in four dissolution media.

The dissolution of the above-mentioned Plain tablet 4 was tested in four dissolution media (water, pH 1.2, pH 4.5 and pH 6.8), and the results were as shown in Table 13 and FIG. 8.

TABLE 13

Test results of the dissolution of Plain tablet 4

| Medium | No. | Time (minutes) | | | | | | | | |
|---|---|---|---|---|---|---|---|---|---|---|
|  |  | 0 | 5 | 10 | 15 | 20 | 30 | 45 | 60 | 90 | 120 |
| $H_2O$ | 4 | 0 | 57 | 92 | 93 | 94 | 95 | 95 | 95 | 96 | 96 |
| pH 1.2 | 4 | 0 | 75 | 96 | 97 | 97 | 97 | 97 | 97 | 97 | 97 |
| pH 4.5 | 4 | 0 | 50 | 97 | 98 | 98 | 99 | 99 | 99 | 99 | 99 |
| pH 6.8 | 4 | 0 | 56 | 83 | 84 | 83 | 83 | 82 | 82 | 81 | 82 |

As could be seen from the results in Tables 12 and 13, as compared with Plain tablet 3B, Plain tablet 4 in which the diluent was replaced with MCC PH200 had increased fluidity of granules and faster disintegration (the disintegration time was shortened from about 11 min to about 4 min); meanwhile, the dissolution was also significantly improved and Plain tablet 4 was capable of achieving rapid and complete dissolution in four media (the plateau level of dissolution was reached after 10 min).

Example 5: Ordinary Tablets (Specification: 240 Mg)

Tabletting was conducted in accordance with Formulations 5A to 5C in Table 14, so as to obtain Plain tablets 5A to 5C.

TABLE 14

Formulation lists of Plain tablets 5A to 5C

| | | Formulation No. 5A | | | | |
|---|---|---|---|---|---|---|
| Name of raw material and excipients | Manufacturer | Batch No. | mg/tablet | wt % | Theoretical amount (g) 100 tablets/batch |
| Inner portion | | | | | |
| API (C-005 citrate) | Self-produced | SLB-F17002 | 332.12[a] | 33.21% | 33.212 |
| microcrystalline cellulose (MCC PH200) | FMC BioPolymer Corporation | PN14827536 | 130.00 | 13.00% | 13.000 |
| crospovidone (PVPP) | Ashland Group Corporation | OOO1926358 | 80.00 | 8.00% | 8.000 |
| magnesium stearate | Faci Chemicals Co., Ltd. | MGS-R0317 | 10.00 | 1.00% | 1.000 |
| Total of inner portion | | | 552.12 | 55.21% | 55.212 |
| Outer portion | | | | | |
| low-substituted hydroxypropyl cellulose (L-HPC) | Shin-Etsu Chemical Co., Ltd. | 6121472 | 50.00 | 5.00% | 5.000 |

TABLE 14-continued

Formulation lists of Plain tablets 5A to 5C

| Name of raw material and excipients | Manufacturer | Batch No. | mg/tablet | wt % | Theoretical amount (g) 100 tablets/ batch |
|---|---|---|---|---|---|
| microcrystalline cellulose (MCC PH200) | FMC BioPolymer Corporation | PN14827536 | 387.88 | 38.79% | 38.788 |
| magnesium stearate | Faci Chemicals Co., Ltd. | MGS-R0317 | 10.00 | 1.00% | 1.000 |
| Total of outer portion | | | 447.88 | 44.79% | 44.788 |
| Total | | | 1000.00 | 100.00% | 100.000 |

Formulation No. 5B

| Name of raw material and excipients | Manufacturer | Batch No. | mg/tablet | wt % | Theoretical amount (g) 100 tablets/ batch |
|---|---|---|---|---|---|
| *Inner portion* | | | | | |
| API (C-005 citrate) | Self-produced | SLB-F17002 | 332.12 | 33.21% | 33.212 |
| colloidal silica ($SiO_2$) | EVONIK Corporation | 156021114 | 30.00 | 3.00% | 3.000 |
| microcrystalline cellulose (MCC PH200) | FMC BioPolymer Corporation | PN14827536 | 100.00 | 10.00% | 10.000 |
| crospovidone (PVPP) | Ashland Group Corporation | OOO1926358 | 80.00 | 8.00% | 8.000 |
| magnesium stearate | Faci Chemicals Co., Ltd. | MGS-R0317 | 10.00 | 1.00% | 1.000 |
| Total of inner portion | | | 552.12 | 55.21% | 55.212 |
| *Outer portion* | | | | | |
| microcrystalline cellulose (MCC PH200) | FMC BioPolymer Corporation | PN14827536 | 437.88 | 43.79% | 43.788 |
| magnesium stearate | Faci Chemicals Co., Ltd. | MGS-R0317 | 10.00 | 1.00% | 1.000 |
| Total of outer portion | | | 447.88 | 44.79% | 44.788 |
| Total | | | 1000.00 | 100.00% | 100.000 |

Formulation No. 5C

| Name of raw material and excipients | Manufacturer | Batch No. | mg/tablet | wt % | Theoretical amount (g) 100 tablets/ batch |
|---|---|---|---|---|---|
| *Inner portion* | | | | | |
| API (C-005 citrate) | Self-produced | SLB-F17002 | 332.12 | 33.21% | 33.212 |
| microcrystalline cellulose (MCC PH200) | FMC BioPolymer Corporation | PN14827536 | 130.00 | 13.00% | 13.000 |
| crospovidone (PVPP) | Ashland Group Corporation | OOO1926358 | 80.00 | 8.00% | 8.000 |
| magnesium stearate | Faci Chemicals Co., Ltd. | MGS-R0317 | 10.00 | 1.00% | 1.000 |
| Total of inner portion | | | 552.12 | 55.21% | 55.212 |

TABLE 14-continued

Formulation lists of Plain tablets 5A to 5C

Outer portion

| | | | | | |
|---|---|---|---|---|---|
| microcrystalline cellulose (MCC PH200) | FMC BioPolymer Corporation | PN14827536 | 437.88 | 43.79% | 43.788 |
| magnesium stearate | Faci Chemicals Co., Ltd. | MGS-R0317 | 10.00 | 1.00% | 1.000 |
| Total of outer portion | | | 447.88 | 44.79% | 44.788 |
| Total | | | 1000.00 | 100.00% | 100.000 |

<sup>a</sup>Equivalent to 240 mg of C-005 in the form of free base

Preparation Processes 5A to 5C (1) The raw material was sieved through an 80-mesh sieve and all excipients were sieved through a 60-mesh sieve for later use.
(2) The formulated amount of the API, the disintegrant for use as the inner portion, and the diluent for use as the inner portion were weighed, charged into the same ziplock bag, uniformly mixed, and then sieved by using a 60-mesh sieve for 3 times.
(3) The formulated amount of the lubricant for use as the inner portion was weighed and charged into the same ziplock bag together with the sieved materials in (2), and the resulting mixture was uniformly mixed.
(4) Dry granulating was carried out. In Preparation process 5A, the pressure was 3 MPa, the feed rate was 12 rpm, and the rolling speed was 18 rpm. In Preparation process 5B, the pressure was 3 MPa, the feed rate was 22 rpm, and the rolling speed was 18 rpm. In Preparation process 5C, the pressure was 3 MPa, the feed rate was 12 rpm, and the rolling speed was 18 rpm.
(5) The resulting mixture was sieved through a 24-mesh sieve.
(6) The formulated amount of the disintegrant for use as the outer portion and the diluent for use as the outer portion were weighed, both of them were charged into the same ziplock bag together with the dry granules, and the resulting mixture was uniformly mixed.
(7) Tabletting was conducted by using a 20*10 mm capsule-shaped punch. The tablet thickness, friability and disintegration time were determined.

TABLE 15

Test results of the tablet thickness, friability, and disintegration time of Plain tablets 5A to 5C

| No. | Tablet weight | Thickness | Hardness | Friability | Disintegration time | Phenomenon during tabletting |
|---|---|---|---|---|---|---|
| 5A | 997 mg | 6.71 mm | 151.1 N | 0.19% | 2 min 33 s | No obvious sticking |
| | 996 mg | 6.71 mm | 152.3 N | | | |
| 5B | 1000 mg | 6.86 mm | 163.2 N | 0.24% | 3 min 3 s | No obvious sticking |
| | 1004 mg | 6.86 mm | 170.2 N | | | |
| 5C | 1014 mg | 6.74 mm | 173.5 N | 0.20% | 4 min 10 s | No obvious sticking |
| | 1010 mg | 6.74 mm | 163.5 N | | | |

Figure 9:
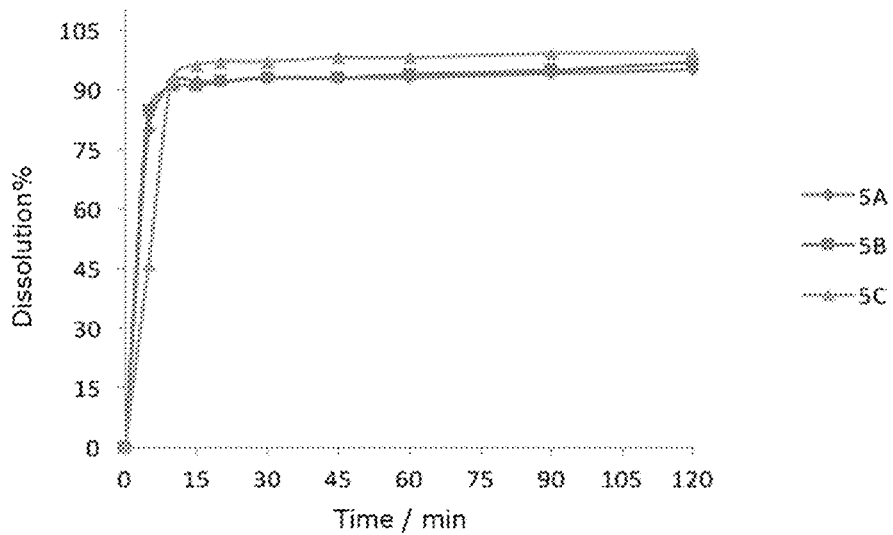
FIG. 9 shows the dissolution profiles of Plain tablets 5A to 5C in a dissolution medium at pH 4.5.
Figure 10:
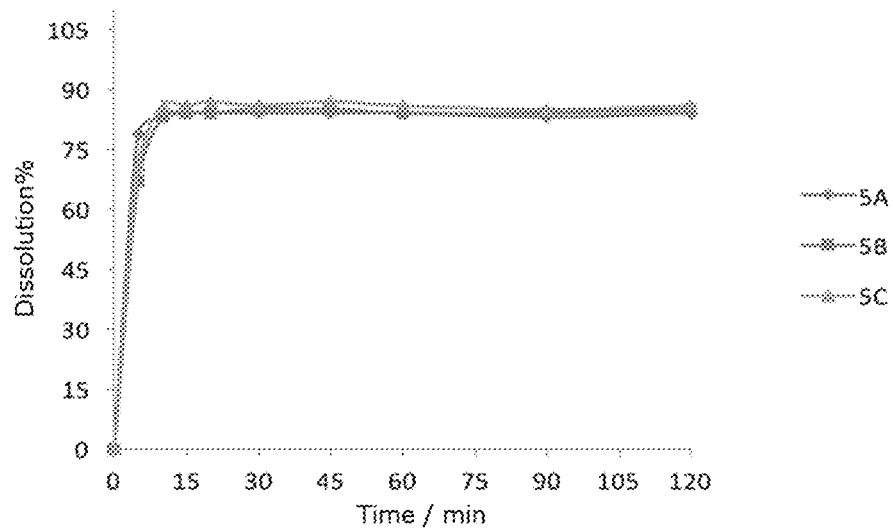
FIG. 10 shows the dissolution profiles of Plain tablets 5A to 5C in a dissolution medium at pH 6.8.

The dissolution of the above-mentioned Plain tablets 5A to 5C was tested in two media (pH 4.5 and pH 6.8), and the results were as shown in Table 16 and FIGS. 9 to 10.

TABLE 16

Test results of the dissolution of Plain tablets 5A to 5C

| | | Time (minutes) | | | | | | | | |
|---|---|---|---|---|---|---|---|---|---|---|
| Medium | No. | 0 | 5 | 10 | 15 | 20 | 30 | 45 | 60 | 90 | 120 |
| pH 4.5 | 5A | 0 | 80 | 92 | 92 | 92 | 93 | 93 | 93 | 94 | 95 |
| | 5B | 0 | 85 | 91 | 91 | 92 | 93 | 93 | 94 | 95 | 97 |
| | 5C | 0 | 46 | 93 | 96 | 97 | 97 | 98 | 98 | 99 | 99 |
| pH 6.8 | 5A | 0 | 79 | 83 | 84 | 84 | 84 | 84 | 84 | 83 | 84 |
| | 5B | 0 | 67 | 83 | 84 | 84 | 85 | 85 | 84 | 84 | 85 |
| | 5C | 0 | 71 | 86 | 86 | 87 | 86 | 87 | 86 | 85 | 86 |

As compared with Formulations 5A and 5B, Formulation 5C comprised neither L-HPC as the disintegrant for use as the outer portion nor colloidal silica as the glidant. As could be seen from the results in Table 15 and Table 16, although the disintegration time of Plain tablet 5C was slightly longer than those of Plain tablets 5A and 5B, all three plain tablets could reach the plateau level of dissolution after 10 minutes, and the dissolution of these three plain tablets had no significant difference.

Example 6: Study on the Formulation and Preparation Process of Ordinary Tablets Comprising Different Amount of Disintegrant Tabletting was conducted in accordance with Formulations 6A to 6C in Table 17, so as to obtain Plain tablets 6A to 6C.

TABLE 17

Formulation lists of Plain tablets 6A to 6C

| Name of raw material and excipients | Manufacturer | Formulation No. 6A (PVPP: 2%) Batch No. | mg/tablet | wt % |
|---|---|---|---|---|
| Inner portion | | | | |
| API (C-005 citrate) | Self-produced | SLB-F17002 | 332.12[a] | 33.21% |
| microcrystalline cellulose (MCC PH200) | FMC BioPolymer Corporation | PN14827536 | 130.00 | 13.00% |
| crospovidone (PVPP) | Ashland Group Corporation | OOO2139987 | 20.00 | 2.00% |
| magnesium stearate | Mallinckrodt Pharmaceuticals | 1611000023 | 10.00 | 1.00% |
| Total of inner portion | | | 492.12 | 49.21% |
| Outer portion | | | | |
| microcrystalline cellulose (MCC PH200) | FMC BioPolymer Corporation | PN14827536 | 497.88 | 49.79% |
| magnesium stearate | Mallinckrodt Pharmaceuticals | 1611000023 | 10.00 | 1.00% |
| Total of outer portion | | | 507.88 | 50.79% |
| Total | | | 1000.00 | 100.00% |

| Name of raw material and excipients | Manufacturer | Formulation No. 6B (PVPP: 5%) Batch No. | mg/tablet | wt % |
|---|---|---|---|---|
| Inner portion | | | | |
| API (C-005 citrate) | Self-produced | SLB-F17002 | 332.12 | 33.21% |
| microcrystalline cellulose (MCC PH200) | FMC BioPolymer Corporation | PN14827536 | 130.00 | 13.00% |
| crospovidone (PVPP) | Ashland Group Corporation | OOO2139987 | 50.00 | 5.00% |
| magnesium stearate | Mallinckrodt Pharmaceuticals | 1611000023 | 10.00 | 1.00% |
| Total of inner portion | | | 522.12 | 52.21% |
| Outer portion | | | | |
| microcrystalline cellulose (MCC PH200) | FMC BioPolymer Corporation | PN14827536 | 467.88 | 46.79% |
| magnesium stearate | Mallinckrodt Pharmaceuticals | 1611000023 | 10.00 | 1.00% |
| Total of outer portion | | | 477.88 | 47.79% |
| Total | | | 1000.00 | 100.00% |

TABLE 17-continued

Formulation lists of Plain tablets 6A to 6C

| Name of raw material and excipients | Formulation No. 6C (PVPP: 10%) | | | |
|---|---|---|---|---|
| | Manufacturer | Batch No. | mg/tablet | wt % |
| Inner portion | | | | |
| API (C-005 citrate) | Self-produced | SLB-F17002 | 332.12 | 33.21% |
| microcrystalline cellulose (MCC PH200) | FMC BioPolymer Corporation | PN14827536 | 130.00 | 13.00% |
| crospovidone (PVPP) | Ashland Group Corporation | OOO2139987 | 100.00 | 10.00% |
| magnesium stearate | Mallinckrodt Pharmaceuticals | 1611000023 | 10.00 | 1.00% |
| Total of inner portion | | | 572.12 | 57.21% |
| Outer portion | | | | |
| microcrystalline cellulose (MCC PH200) | FMC BioPolymer Corporation | PN14827536 | 417.88 | 41.79% |
| magnesium stearate | Mallinckrodt Pharmaceuticals | 1611000023 | 10.00 | 1.00% |
| Total of outer portion | | | 427.88 | 42.79% |
| Total | | | 1000.00 | 100.00% |

<sup>a</sup>Equivalent to 240 mg of C-005 in the form of free base

Preparation Processes 6A to 6C (1) The raw material was sieved through an 80-mesh sieve and all excipients were sieved through a 60-mesh sieve for later use.
(2) The formulated amount of the API, the disintegrant, and the diluent for use as the inner portion were weighed, charged into the same ziplock bag, uniformly mixed, and then sieved by using a 60-mesh sieve for 3 times.
(3) The formulated amount of the lubricant for use as the inner portion was weighed and charged into the same ziplock bag together with the sieved materials in (2), and the resulting mixture was uniformly mixed.
(4) Dry granulating was carried out. In Preparation process 6A, the pressure was 3 MPa, the feed rate was 13 rpm, and the rolling speed was 18 rpm. In Preparation process 6B, the pressure was 3 MPa, the feed rate was 13 rpm, and the rolling speed was 18 rpm. In Preparation process 6C, the pressure was 3 MPa, the feed rate was 12 rpm, and the rolling speed was 18 rpm.
(5) The resulting mixture was sieved through a 24-mesh sieve.
(6) The formulated amount of the diluent for use as the outer portion was weighed and charged into the same ziplock bag together with the dry granules, and the resulting mixture was uniformly mixed.
(7) The formulated amount of the lubricant for use as the outer portion was weighed, charged into the same ziplock bag and uniformly mixed with the mixture therein.
(8) Tabletting was conducted by using Gylongli ZP-10A tablet machine and a 20*10 mm capsule-shaped punch. The tablet thickness, friability and disintegration time were determined.

TABLE 18

Test results of the tablet thickness, friability, and disintegration time of Plain tablets 6A to 6C

| Batch No. | Tablet weight | Thickness | Hardness | Friability | Disintegration time | Phenomenon during tabletting |
|---|---|---|---|---|---|---|
| 6A | 1004 mg | 6.92 mm | 159.9 N | 0.17% | 3 min 53 s | No obvious sticking |
| 6B | 1001 mg | 6.75 mm | 157.1 N | 0.24% | 2 min 55 s | No obvious sticking |
| 6C | 1004 mg | 6.74 mm | 166.6 N | 0.17% | 2 min 40 s | No obvious sticking |

As could be seen from the results in Table 18, the disintegration time of the plain tablet would be gradually shortened with the increase of the amount of disintegrant in the formulation, however, when the amount of disintegrant reached 5% or more, the amplitude of variation of the disintegration time of the plain tablet would be gradually decreased.

Figure 11:
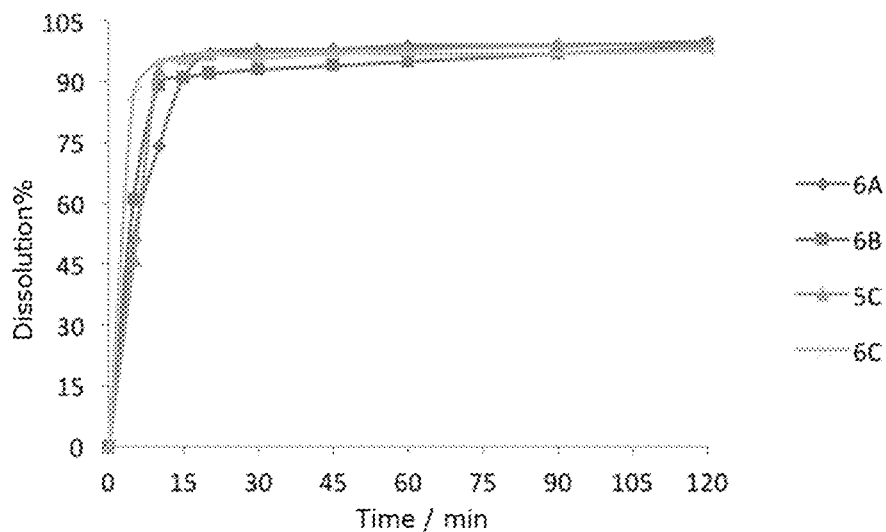
FIG. 11 shows the dissolution profiles of Plain tablets 6A to 6C and Plain tablet 5C in a dissolution medium at pH 4.5.
Figure 12:
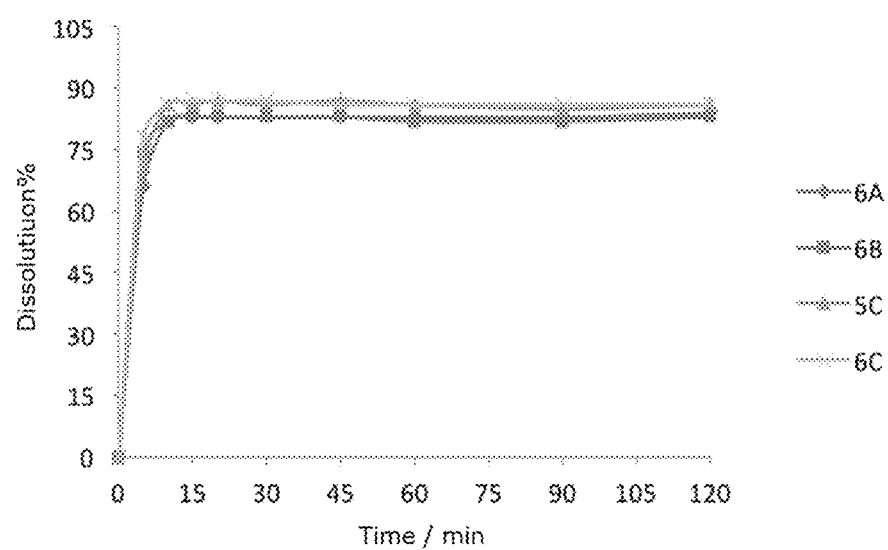
FIG. 12 shows the dissolution profiles of Plain tablets 6A to 6C and Plain tablet 5C in a dissolution medium at pH 6.8.

The dissolution of the above-mentioned Plain tablets 6A to 6C was tested in two media (pH 4.5 and pH 6.8), and the results were as shown in Table 19 and FIGS. 11 to 12.

TABLE 19

Test results of the dissolution of Plain tablets 6A to 6C (Plain tablet 5C was tested together)

| Medium | No. | Time (minutes) | | | | | | | | | |
|---|---|---|---|---|---|---|---|---|---|---|---|
| | | 0 | 5 | 10 | 15 | 20 | 30 | 45 | 60 | 90 | 120 |
| pH 4.5 | 6A (PVPP: 2%) | 0 | 51 | 74 | 91 | 97 | 98 | 98 | 99 | 99 | 100 |
| | 6B (PVPP: 5%) | 0 | 61 | 89 | 91 | 92 | 93 | 94 | 95 | 97 | 99 |
| | 5C (PVPP: 8%) | 0 | 46 | 93 | 96 | 97 | 97 | 98 | 98 | 99 | 99 |
| | 6C (PVPP: 10%) | 0 | 87 | 95 | 95 | 97 | 96 | 97 | 97 | 97 | 98 |
| pH 6.8 | 6A (PVPP: 2%) | 0 | 66 | 82 | 83 | 83 | 83 | 83 | 83 | 83 | 84 |
| | 6B (PVPP: 5%) | 0 | 74 | 82 | 83 | 83 | 83 | 83 | 82 | 82 | 83 |
| | 5C (PVPP: 8%) | 0 | 71 | 86 | 86 | 87 | 86 | 87 | 86 | 85 | 86 |
| | 6C (PVPP: 10%) | 0 | 78 | 86 | 87 | 87 | 87 | 86 | 86 | 86 | 86 |

As could be seen from the results in Table 19, in the medium at pH 4.5, when the amount of disintegrant reached 8% or more, the plain tablet could reach the plateau level of dissolution after 10 minutes and achieve a dissolution percentage of approximately 95%; while in the medium at pH 6.8, when the amount of disintegrant reached 8% or more, the plain tablet could reach the plateau level of dissolution after 10 minutes and achieve a dissolution percentage of approximately 85%.

Example 7: Ordinary Tablets in which the Lubricant was Added in Different Manners Tabletting was conducted in accordance with Formulation 7 in Table 20, so as to obtain Plain tablet 7.

TABLE 20

Formulation list of Plain tablet 7

| Name of raw material and excipients | Formulation No. 7 (Inner lubricant: 2%, Outer lubricant: 0.5%) | | | |
|---|---|---|---|---|
| | Manufacturer | Batch No. | mg/tablet | wt % |
| Inner portion | | | | |
| API (C-005 citrate) | Self-produced | SLB-F17002 | 332.12$^a$ | 33.21% |
| microcrystalline cellulose (MCC PH200) | FMC BioPolymer Corporation | PN16829974 | 130.00 | 13.00% |
| crospovidone (PVPP) | Ashland Group Corporation | OOO2139987 | 80.00 | 8.00% |
| magnesium stearate | Mallinckrodt Pharmaceuticals | 1611000023 | 20.00 | 2.00% |
| Total of inner portion | | | 562.12 | 56.21% |

TABLE 20-continued

Formulation list of Plain tablet 7

| Name of raw material and excipients | Formulation No. 7 (Inner lubricant: 2%, Outer lubricant: 0.5%) | | | |
|---|---|---|---|---|
| | Manufacturer | Batch No. | mg/tablet | wt % |
| Outer portion | | | | |
| microcrystalline cellulose (MCC PH200) | FMC BioPolymer Corporation | PN16829974 | 432.88 | 43.29% |
| magnesium stearate | Mallinckrodt Pharmaceuticals | 1611000023 | 5.00 | 0.50% |
| Total of outer portion | | | 437.88 | 43.79% |
| Total of inner and outer portion | | | 1000.00 | 100.00% |

<sup>a</sup>Equivalent to 240 mg of C-005 in the form of free base

Preparation Process 7

(1) The raw material was sieved through an 80-mesh sieve and all excipients were sieved through a 60-mesh sieve for later use.
(2) The formulated amount of the API, the disintegrant, and the diluent for use as the inner portion were weighed, charged into the same ziplock bag and uniformly mixed.
(3) The formulated amount of the lubricant for use as the inner portion was weighed and charged into the same ziplock bag together with the sieved materials in (2), and the resulting mixture was uniformly mixed.
(4) Dry granulating was carried out with a pressure of 3 MPa, a feed rate of 13 rpm, and a rolling speed of 18 rpm.
(5) The resulting mixture was sieved through a 24-mesh sieve.
(6) The formulated amount of the diluent for use as the outer portion was weighed and charged into the same ziplock bag together with the dry granules, and the resulting mixture was uniformly mixed.
(7) The formulated amount of the lubricant for use as the outer portion was weighed, charged into the same ziplock bag and uniformly mixed with the mixture therein.
(8) Tabletting was conducted by using Gylongli ZP-10A tablet machine and a 20*10 mm capsule-shaped punch. The tablet thickness, friability, and disintegration time were determined.

TABLE 21

Test results of the tablet thickness, friability, and disintegration time of Plain tablet 7

| No. | Tablet weight | Thickness | Hardness | Friability | Disintegration time | Phenomenon during tabletting |
|---|---|---|---|---|---|---|
| 7 | 1002 mg | 6.5 mm | 169.6 N | 0.09% | 6 min 25 s | No obvious sticking |
| | 1002 mg | 6.5 mm | 169.9 N | | | |

As could be seen from the results in Table 21, as compared with Plain tablet 5C in which the amount of lubricant for use as the inner portion was equal to that for use as the outer portion, the disintegration time of Plain tablet 7 was increased by 2 minutes or so. It could be seen that a formulation in which the amount of lubricant for use as the inner portion was four times of that for use as the outer portion would prolong the disintegration process.

Figure 13:
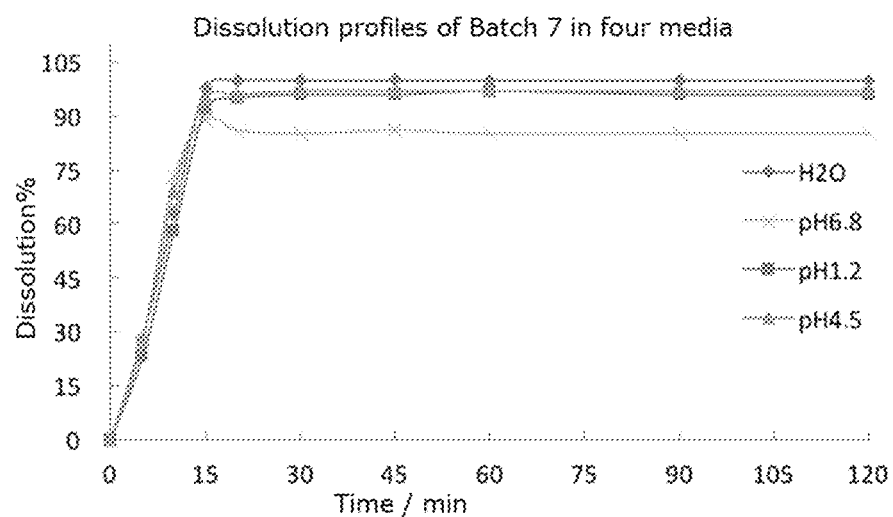
FIG. 13 shows the dissolution profiles of Plain tablet 7 in four dissolution media.

The dissolution of the above-mentioned Plain tablet 7 was tested in four dissolution media (water, pH 1.2, pH 4.5 and pH 6.8), and the results were as shown in Table 22 and FIG. 13.

TABLE 22

Test results of the dissolution of Plain tablet 7

| Medium | No. | Time (minutes) | | | | | | | | |
|---|---|---|---|---|---|---|---|---|---|---|
| | | 0 | 5 | 10 | 15 | 20 | 30 | 45 | 60 | 90 | 120 |
| H$_2$O | 7 | 0 | 28 | 63 | 98 | 100 | 100 | 100 | 100 | 100 | 100 |
| pH 1.2 | 7 | 0 | 23 | 58 | 92 | 95 | 96 | 96 | 97 | 96 | 96 |
| pH 4.5 | 7 | 0 | 28 | 69 | 95 | 96 | 97 | 97 | 97 | 97 | 97 |
| pH 6.8 | 7 | 0 | 27 | 73 | 89 | 86 | 85 | 86 | 85 | 85 | 85 |

As could be seen from the results in Table 22, as compared with Plain tablet 5C in which the amount of lubricant for use as the inner portion was equal to that for use as the outer portion, Plain tablet 7 could reach the plateau level of dissolution at about 15 minutes in the four media and achieve a dissolution percentage of 85% or more, and the dissolution effect was significantly superior to that of Plain tablet 5C.

Example 8: Coated Tablets

Coated tablets 8A to 8C were prepared and obtained in accordance with Formulations 8A to 8C in Table 23.

TABLE 23

Formulation lists of Coated tablets 8A to 8C

| Name of raw material and excipients | Formulation No. 8A (900 tablets in theory) | | | |
|---|---|---|---|---|
| | Manufacturer | Batch No. | mg/tablet | wt % |
| Inner portion | | | | |
| API (C-005 citrate) | Self-produced | SLB-F180102 | 332.12[a] | 33.21% |
| microcrystalline cellulose (MCC PH200) | FMC BioPolymer Corporation | PN16829974 | 130.00 | 13.00% |
| crospovidone (PVPP) | Ashland Group Corporation | OOO2139987 | 80.00 | 8.00% |
| magnesium stearate | Mallinckrodt Pharmaceuticals | 1611000023 | 20.00 | 2.00% |
| Total of inner portion | | | 562.12 | 56.21% |
| Outer portion | | | | |
| microcrystalline cellulose (MCC PH200) | FMC BioPolymer Corporation | PN16829974 | 432.88 | 43.29% |
| magnesium stearate | Mallinckrodt Pharmaceuticals | 1611000023 | 5.00 | 0.50% |
| Total of outer portion | | | 437.88 | 43.79% |
| Total | | | 1000.00 | 100.00% |

| Name of raw material and excipients | Formulation No. 8B (900 tablets in theory) | | | |
|---|---|---|---|---|
| | Manufacturer | Batch No. | mg/tablet | wt % |
| Inner portion | | | | |
| API (C-005 citrate) | Self-produced | SLB-F180103 | 332.12 | 33.21% |
| microcrystalline cellulose (MCC PH200) | FMC BioPolymer Corporation | PN16829974 | 130.00 | 13.00% |

TABLE 23-continued

Formulation lists of Coated tablets 8A to 8C

| | | | | |
|---|---|---|---|---|
| crospovidone (PVPP) | Ashland Group Corporation | OOO2139987 | 80.00 | 8.00% |
| magnesium stearate | Mallinckrodt Pharmaceuticals | 1611000023 | 20.00 | 2.00% |
| Total of inner portion | | | 562.12 | 56.21% |
| Outer portion | | | | |
| microcrystalline cellulose (MCC PH200) | FMC BioPolymer Corporation | PN16829974 | 432.88 | 43.29% |
| magnesium stearate | Mallinckrodt Pharmaceuticals | 1611000023 | 5.00 | 0.50% |
| Total of outer portion | | | 437.88 | 43.79% |
| Total | | | 1000.00 | 100.00% |

| Name of raw material and excipients | Formulation No. 6C (1600 tablets in theory) | | | |
|---|---|---|---|---|
| | Manufacturer | Batch No. | mg/tablet | wt % |
| Inner portion | | | | |
| API (C-005 citrate) | Self-produced | SLB-F180102 | 83.03 | 33.21% |
| microcrystalline cellulose (MCC PH200) | FMC BioPolymer Corporation | PN16829974 | 32.50 | 13.00% |
| crospovidone (PVPP) | Ashland Group Corporation | OOO2139987 | 20.00 | 8.00% |
| magnesium stearate | Mallinckrodt Pharmaceuticals | 1611000023 | 5.00 | 2.00% |
| Total of inner portion | | | 140.53 | 56.21% |
| Outer portion | | | | |
| microcrystalline cellulose (MCC PH200) | FMC BioPolymer Corporation | PN16829974 | 108.22 | 43.29% |
| magnesium stearate | Mallinckrodt Pharmaceuticals | 1611000023 | 1.25 | 0.50% |
| Total of outer portion | | | 109.47 | 43.79% |
| Total | | | 250.00 | 100.00% |

[a] Equivalent to 240 mg of C-005 in the form of free base

Preparation Processes 8A to 8C (1) The raw material was sieved through an 80-mesh sieve and all excipients were sieved through a 60-mesh sieve for later use.
(2) The formulated amount of the API, the disintegrant, and the diluent for use as the inner portion were weighed and charged into a mixer with a rotating speed of 15 rpm, and the resulting mixture was mixed for 10 min.
(3) The formulated amount of the lubricant for use as the inner portion was weighed and charged into a mixer with a rotating speed of 15 rpm, and the resulting mixture was mixed for 5 min.
(4) Dry granulating was carried out with a pressure of 3 MPa, a feed rate of 9 rpm, and a rolling speed of 22 rpm. A 1.0 mm sieve was used for sorting, and the speed of sorting was 50 rpm.
(5) The formulated amount of the diluent for use as the outer portion was weighed and charged into a mixer together with the dry granules, the rotating speed was 15 rpm, and the resulting mixture was mixed for 10 min.
(6) The formulated amount of the lubricant for use as the outer portion was weighed and charged into a mixer with a rotating speed of 15 rpm, and the resulting mixture was mixed for 5 min.
(7) Tabletting was conducted by using Gylongli ZP-10A tablet machine. A 20*10 mm capsule-shaped punch was used for tabletting in Preparation processes 8A and 8B and a 9 mm shallow arc punch was used for tabletting in Preparation process 8C, so as to obtain Plain tablets 8A to 8C. The friability and the disintegration time were determined.
(8) Plain tablets 8A to 8C were coated with Opadry 85G640044 series coating material (Colorcon Corporation, Batch No.: THL46201, solid content: 15%), the target coating weight gain was 3%, and Coated tablets 8A to 8C were obtained. The dissolution of Coated tablets 8A to 8C was determined.

TABLE 24

Test results of the friability and the disintegration time of Plain tablets 8A to 8C

| No. | Friability | Disintegration time | Phenomenon during tabletting |
|---|---|---|---|
| 8A | 0.21% | 2 min 2 s | No obvious sticking |
| 8B | 0.07% | 3 min | No obvious sticking |
| 8C | 0.00% | 1 min 33 s | No obvious sticking |

Figure 14:
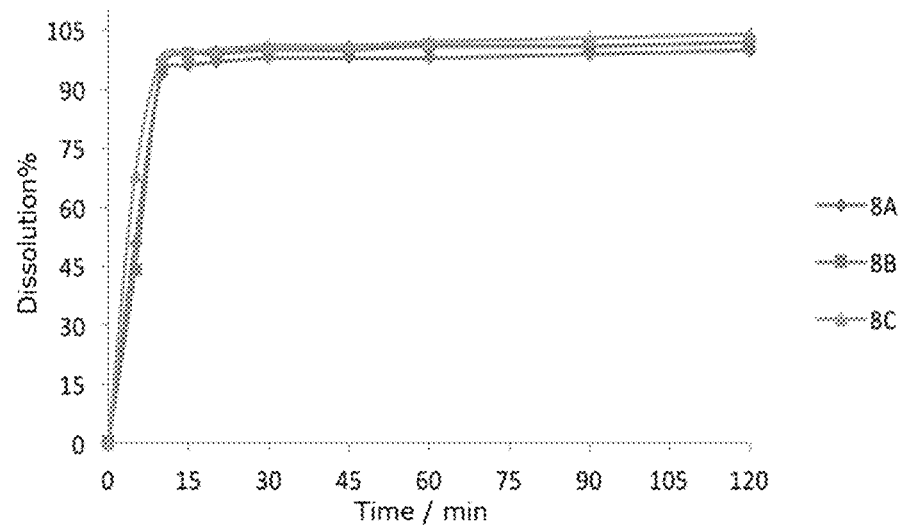
FIG. 14 shows the dissolution profiles of Coated tablets 8A to 8C in a dissolution medium at pH 4.5.
Figure 15:
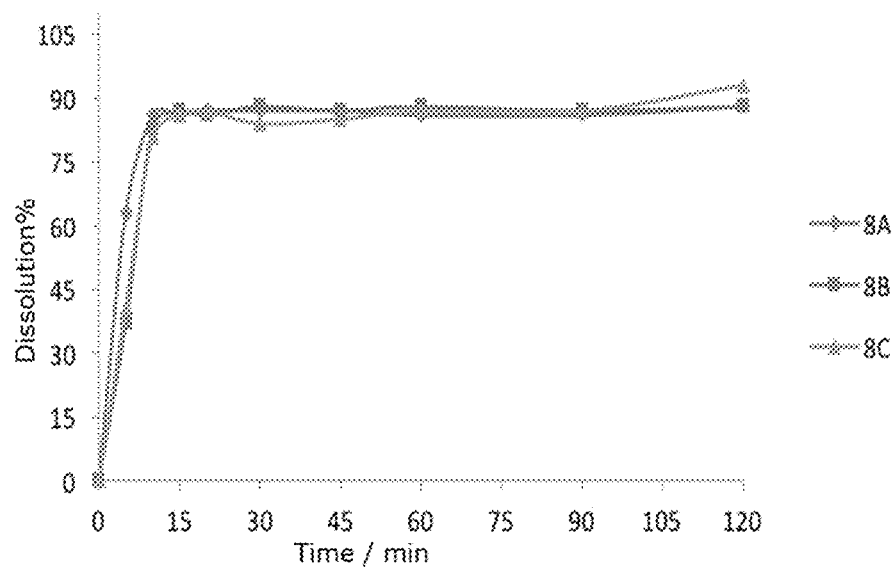
FIG. 15 shows the dissolution profiles of Coated tablets 8A to 8C in a dissolution medium at pH 6.8.

The dissolution of the above-mentioned Coated tablets 8A to 8C was tested in two media (pH 4.5 and pH 6.8), and the results were as shown in Table 25 and FIGS. 14 to 15.

TABLE 25

Test results of the dissolution of Coated tablets 8A to 8C

| Medium | No. | Time (minutes) | | | | | | | | |
|---|---|---|---|---|---|---|---|---|---|---|
| | | 0 | 5 | 10 | 15 | 20 | 30 | 45 | 60 | 90 | 120 |
| pH 4.5 | 8A | 0 | 51 | 94 | 96 | 97 | 98 | 98 | 98 | 99 | 100 |
| | 8B | 0 | 44 | 96 | 99 | 99 | 100 | 100 | 101 | 101 | 102 |
| | 8C | 0 | 68 | 98 | 99 | 100 | 101 | 101 | 102 | 103 | 104 |
| pH 6.8 | 8A | 0 | 63 | 86 | 86 | 87 | 87 | 87 | 86 | 86 | 88 |
| | 8B | 0 | 37 | 83 | 87 | 86 | 88 | 87 | 88 | 87 | 88 |
| | 8C | 0 | 41 | 81 | 86 | 87 | 84 | 85 | 87 | 87 | 93 |

As could be seen from the results in Table 25, Coated tablets 8A to 8C could reach the plateau level of dissolution at about 10 to 15 minutes in both media, at least achieve a dissolution percentage of 85% and exhibit good dissolution behavior.

Comparative Example: A Blend in Capsule

In the previous research process, C-005 citrate and microcrystalline cellulose were once blended at a weight ratio of 1:2 and filled into a non-transparent white HPMC capsule shell (size 0#) to prepare a blend in capsule. The filling amount was approximately 60 mg of C-005 in the form of free base in each capsule, and the formulation list was as shown in Table 26.

TABLE 26

Formulation list of the blend in capsule

| | | Formulation No. 1A (Specification: 60 mg) | | | |
|---|---|---|---|---|---|
| Name of raw material and excipients | Manufacturer | Batch No. | mg/capsule | wt % | Theoretical amount (g) 100 tablets/batch |
| API (C-005 citrate) | Self-produced | SLB-F170829 | 83.03[a] | 33.33% | 8.30 |
| microcrystalline cellulose (MCC PH102) | JRS Pharma | 5610264526 | 166.06 | 66.67% | 16.61 |
| Total | | | 249.09 | 100% | 24.91 |

[a]Equivalent to 60 mg of C-005 in the form of free base

Figure 16:
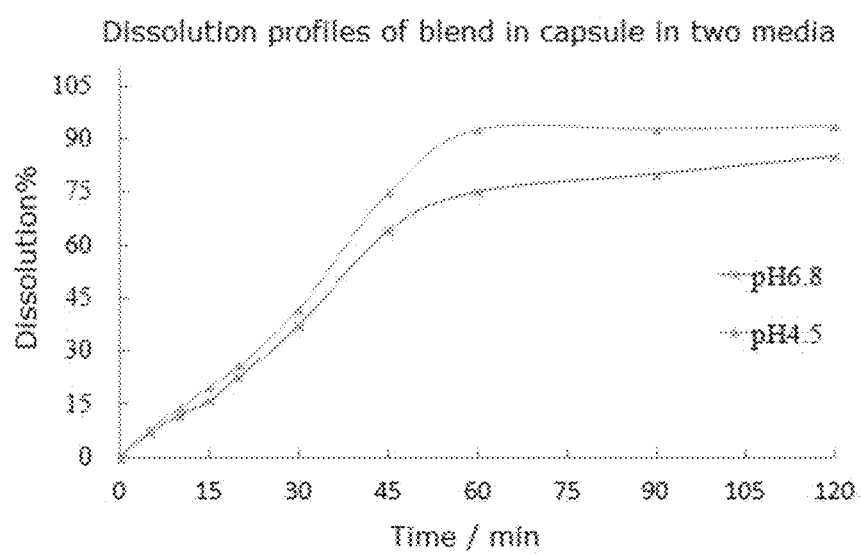
FIG. 16 shows the dissolution profiles of a blend in capsule in a dissolution medium at pH 4.5 and a dissolution medium at pH 6.8.

The dissolution of the above-mentioned blend in capsule was tested in two media (pH 4.5 and pH 6.8), and the results were as shown in Table 27 and FIG. 16.

TABLE 27

Test results of the dissolution of the blend in capsule

| Medium | No. | Time (minutes) | | | | | | | | |
|---|---|---|---|---|---|---|---|---|---|---|
| | | 0 | 5 | 10 | 15 | 20 | 30 | 45 | 60 | 90 | 120 |
| pH 4.5 | 10 | 0.0 | 8 | 14 | 20 | 26 | 42 | 75 | 93 | 93 | 94 |
| pH 6.8 | 10 | 0 | 7 | 12 | 16 | 23 | 37 | 64 | 75 | 80 | 85 |

As could be seen from the results in Table 27, in the medium at pH 6.8, only a release percentage of 37% was achieved after 30 minutes, 75% was achieved after 60 minutes, and 85% was basically achieved after 120 minutes. In the medium at pH 4.5, a release percentage of 75% was achieved after 45 minutes, and 93% was basically achieved after 60 minutes. As compared with the tablets in the aforementioned Examples, the dissolution of the blend in capsule was not satisfactory, and it was difficult to reduce or avoid risks caused by the inter-dose and/or inter-patient variability of absorption. By contrast, the pharmaceutical tablet of the present disclosure was exactly capable of solving the above-mentioned problems and was suitable for the follow-up drug development.

What is claimed is:

1. A pharmaceutical composition comprising:
   (a) from 3 to 70 parts of a pharmaceutical substance;
   (b) from 5 to 95 parts of one or more pharmaceutical diluents;
   (c) from 0.5 to 45 parts of one or more pharmaceutical disintegrants;
   (d) from 0 to 5 parts of one or more pharmaceutical solubilizers; and
   (e) from 0 to 5 parts of one or more pharmaceutical lubricants;
   wherein all parts are by weight and a sum of these parts in (a), (b), (c), (d) and (e) is 100; and
   wherein the pharmaceutical substance is N-(2-((2-(dimethylamino)ethyl)(methyl)amino)-4-methoxy-5-((4-(1-methyl-1H-pyrrolo[3,2-b]pyridin-3-yl)pyrimidin-2-yl)amino)phenyl)acrylamide citrate;
   the one or more pharmaceutical diluents is selected from any one or more of microcrystalline cellulose, calcium phosphate, calcium sulfate cellulose acetate (or referred to as acetyl cellulose), ethyl cellulose, erythritol, fructose inulin isomaltitol, lactitol lactose maltitol maltodextrin, maltose mannitol, sorbitol polydextrose, polyethylene glycol, starch sucrose trehalose, and xylitol;
   the one or more pharmaceutical disintegrants is selected from the group consisting of alginic acid, calcium alginate, sodium alginate, chitosan, calcium carboxymethylcellulose (CMC-Ca), sodium carboxymethylcellulose (CMC-Na), croscarmellose sodium (CCNa), povidone (PVP), crospovidone (crosslinked polyvinylpyrrolidone; PVPP), guar gum, low-substituted hydroxypropyl cellulose (L-HPC), sodium carboxymethyl starch (CMS-Na), colloidal silica (micronized silica gel; $SiO_2$), and starch.

2. The pharmaceutical composition according to claim 1, wherein
   the pharmaceutical composition comprises from 5 to 60 parts of the pharmaceutical substance.

3. The pharmaceutical composition according to claim 1, wherein
   the pharmaceutical composition comprises from 10 to 85 parts of the one or more pharmaceutical diluents.

4. The pharmaceutical composition according to claim 1, wherein
   when the pharmaceutical diluent consists of one component, said one component is microcrystalline cellulose; and when the pharmaceutical diluent consists of multiple components, one of said multiple components is microcrystalline cellulose, and microcrystalline cellulose constitutes from 10 wt % to 90 wt % of the pharmaceutical diluent.

5. The pharmaceutical composition according to claim 1, wherein
   a) when the pharmaceutical disintegrant consists of one component, said one component is crospovidone; and when the pharmaceutical disintegrant consists of multiple components, one of said multiple components is crospovidone, and crospovidone constitutes from 10 wt % to 90 wt % of the pharmaceutical disintegrant;
   b) when the pharmaceutical disintegrant consists of one component, said one component is low-substituted hydroxypropyl cellulose; and when the pharmaceutical disintegrant consists of multiple components, one of said multiple components is low-substituted hydroxypropyl cellulose, and low-substituted hydroxypropyl cellulose constitutes from 10 wt % to 90 wt % of the pharmaceutical disintegrant;
   c) when the pharmaceutical disintegrant consists of one component, said one component is sodium carboxymethyl starch; and when the pharmaceutical disintegrant consists of multiple components, one of said multiple components is sodium carboxymethyl starch and sodium carboxymethyl starch constitutes from 10 wt % to 50 wt % of the pharmaceutical disintegrant; or
   d) when the pharmaceutical disintegrant consists of one component, said one component is colloidal silica; and when the pharmaceutical disintegrant consists of multiple components, one of said multiple components is colloidal silica and colloidal silica constitutes from 10 wt % to 50 wt % of the pharmaceutical disintegrant.

6. The pharmaceutical composition according to claim 1, wherein
   the pharmaceutical composition comprises from 0 to 3 parts of one or more pharmaceutical solubilizers (d).

7. The pharmaceutical composition according to claim 1, wherein
   the solubilizer is selected from any one or more of benzalkonium chloride, benzyl benzoate, cetylpyridinium chloride (CPC), cyclodextrin, diethylene glycol monoethyl ether, lecithin, oleyl alcohol, poloxamer, sodium lauryl sulfate (SLS), sorbitan tristearate (ST), and glyceryl trioleate.

8. The pharmaceutical composition according to claim 1, wherein
   when the pharmaceutical solubilizer consists of one component, said one component is sodium lauryl sulfate; and when the pharmaceutical solubilizer consists of multiple components, one of said multiple components is sodium lauryl sulfate, and sodium lauryl sulfate constitutes from 10 wt % to 90 wt % of the pharmaceutical solubilizer.

9. The pharmaceutical composition according to claim 1, wherein
   the pharmaceutical composition comprises from 0 to 4 parts of the one or more pharmaceutical lubricants.

10. The pharmaceutical composition according to claim 1, wherein
    the lubricant is selected from any one or more of stearic acid, magnesium stearate, sodium stearate, calcium stearate, zinc stearate, glyceryl behenate, glyceryl dibehenate, glyceryl tribehenate, glyceryl monostearate, glyceryl distearate, glyceryl tristearate, myristic acid, palmitic acid, sodium stearyl fumarate, and talc.

11. A pharmaceutical tablet comprising a tablet core, wherein the tablet core comprises the pharmaceutical composition according to claim 1, wherein the tablet core optionally has a coating.

12. A method for treating lung cancer, comprising a step of administering to a subject in need thereof a therapeutically effective amount of the pharmaceutical composition according to claim 1.

13. A method for treating lung cancer, comprising a step of administering to a subject in need thereof a therapeutically effective amount of the tablet according to claim 11.

14. A pharmaceutical composition comprising
(a) from 10 to 45 parts of a pharmaceutical substance which is N-(2-((2-(dimethylamino)ethyl)(methyl) amino)-4-methoxy-5-((4-(1-methyl-1H-pyrrolo[3,2-b] pyridin-3-yl)pyrimidin-2-yl)amino)phenyl)acrylamide or a pharmaceutically acceptable salt thereof;
(b) from 30 to 70 parts of one or more pharmaceutical diluents;
(c) from 0.5 to 45 parts of one or more pharmaceutical disintegrants;
(d) from 0 to 5 parts of one or more pharmaceutical solubilizers; and
(e) from 0 to 5 parts of one or more pharmaceutical lubricants;
wherein all parts are parts by weight and a sum of these parts in (a), (b), (c), (d) and (e) is 100 parts by weight.

15. The pharmaceutical composition of claim 14, wherein the pharmaceutical substance is present as the citrate salt; and
the parts of the one or more pharmaceutical diluents is 40 to 70 parts, wherein a) when the pharmaceutical diluent consists of one component, said one component is microcrystalline cellulose; and b) when the pharmaceutical diluent consists of multiple components, one of said multiple components is microcrystalline cellulose, and microcrystalline cellulose constitutes from 10 wt % to 90 wt % of the pharmaceutical diluent.

16. The pharmaceutical composition of claim 15, wherein
a) when the pharmaceutical disintegrant consists of one component, said one component is crospovidone; and when the pharmaceutical disintegrant consists of multiple components, one of said multiple components is crospovidone, and crospovidone constitutes from 10 wt % to 90 wt % of the pharmaceutical disintegrant;
b) when the pharmaceutical disintegrant consists of one component, said one component is low-substituted hydroxypropyl cellulose; and when the pharmaceutical disintegrant consists of multiple components, one of said multiple components is low-substituted hydroxypropyl cellulose, and low-substituted hydroxypropyl cellulose constitutes from 10 wt % to 90 wt % of the pharmaceutical disintegrant;
c) when the pharmaceutical disintegrant consists of one component, said one component is sodium carboxymethyl starch; and when the pharmaceutical disintegrant consists of multiple components, one of said multiple components is sodium carboxymethyl starch, and sodium carboxymethyl starch constitutes from 10 wt % to 50 wt % of the pharmaceutical disintegrant; or
d) when the pharmaceutical disintegrant consists of one component, said one component is colloidal silica; and when the pharmaceutical disintegrant consists of multiple components, one of said multiple components is colloidal silica, and colloidal silica constitutes from 10 wt % to 50 wt % of the pharmaceutical disintegrant.

17. A tablet comprising the pharmaceutical composition of claim 14, wherein the tablet comprises a compressed mixture of a) granules comprising the pharmaceutical substance, the one or more pharmaceutical diluents, the one or more pharmaceutical disintegrants, the one or more pharmaceutical lubricants; and b) a mixture of the one or more pharmaceutical diluents, the one or more pharmaceutical disintegrants, and the one or more pharmaceutical lubricants.

18. The pharmaceutical composition of claim 1, wherein
the one or more pharmaceutical diluents is selected from the group consisting of microcrystalline cellulose, isomaltitol, lactitol, lactose, mannitol, sorbitol, and polydextrose;
the one or more pharmaceutical disintegrants is selected from the group consisting of low-substituted hydroxypropyl cellulose (L-HPC), sodium carboxymethyl starch (CMS-Na), crospovidone (crosslinked polyvinylpyrrolidone; PVPP), croscarmellose sodium (CCNa), and colloidal silica (micronized silica gel; $SiO_2$);
the one or more pharmaceutical solubilizers is present and is selected from the group consisting of sodium lauryl sulfate (SLS), cetylpyridinium chloride (CPC), and sorbitan tristearate (ST); and
the one or more pharmaceutical lubricants is present and is selected from the group consisting of magnesium stearate, calcium stearate, myristic acid, palmitic acid, and sodium stearyl fumarate.

19. A tablet comprising the pharmaceutical composition of claim 18, wherein the tablet comprises a compressed mixture of a) granules comprising the pharmaceutical substance, the one or more pharmaceutical diluents, the one or more pharmaceutical disintegrants, the one or more pharmaceutical lubricants; and b) a mixture of the one or more pharmaceutical diluents, the one or more pharmaceutical disintegrants, and the one or more pharmaceutical lubricants.

* * * * *